United States Patent
Ballard et al.

(10) Patent No.: US 6,447,808 B2
(45) Date of Patent: Sep. 10, 2002

(54) GROWTH-PROMOTING AGENT

(75) Inventors: Francis John Ballard, Kensington; Geoffrey Leonard Francis, Athelstone; Geoffrey Owen Regester, Ferntree Gully; Leanna Christine Read, Kensington; David Andrew Belford, Seacliff Park, all of (AU)

(73) Assignee: GroPep Limited, Thebarton (AU)

( * ) Notice: Subject to any disclaimer, the term of this patent is extended or adjusted under 35 U.S.C. 154(b) by 0 days.

(21) Appl. No.: 09/912,040

(22) Filed: Jul. 24, 2001

Related U.S. Application Data

(60) Division of application No. 09/082,987, filed on May 22, 1998, now Pat. No. 6,319,522, which is a division of application No. 08/641,754, filed on May 2, 1996, now abandoned, and a continuation-in-part of application No. 08/814,833, filed on Mar. 11, 1997, now abandoned, which is a continuation-in-part of application No. 07/956,759, filed as application No. PCT/AU91/00303 on Jul. 9, 1991, now Pat. No. 5,866,418.

(30) Foreign Application Priority Data

Jul. 13, 1990 (AU) ................................................ 1170/90
May 2, 1995 (AU) ................................................ 2712/95

(51) Int. Cl.[7] .............................................. A61K 35/20
(52) U.S. Cl. ...................... 424/535; 530/350; 530/399; 530/416
(58) Field of Search ...................... 424/535; 530/350, 530/399, 416

(56) References Cited

U.S. PATENT DOCUMENTS

| | | | | | |
|---|---|---|---|---|---|
| 3,969,337 | A | * | 7/1976 | Laurer et al. | 530/416 |
| 4,440,860 | A | * | 4/1984 | Klagsbrun | 435/384 |
| 4,668,771 | A | * | 5/1987 | Kawakami et al. | 530/366 |
| 4,783,524 | A | * | 11/1988 | Larsen et al. | 530/350 |
| 4,791,193 | A | * | 12/1988 | Okonogi et al. | 530/416 |
| 5,055,558 | A | * | 10/1991 | Chianacone et al. | 530/386 |
| 5,221,734 | A | * | 6/1993 | Bürk et al. | 530/399 |
| 5,500,229 | A | * | 3/1996 | Aalto et al. | 424/535 |

FOREIGN PATENT DOCUMENTS

| | | |
|---|---|---|
| AU | 67992/74 | 4/1974 |
| AU | 83720/82 | 11/1982 |
| AU | 52480/86 | 2/1985 |
| AU | 49227/85 | 6/1986 |
| AU | 23326/88 | 9/1988 |
| EP | 0 219 372 | * 6/1986 |
| EP | 0 253 395 | * 7/1987 |
| EP | 0 285 576 | * 3/1988 |
| EP | 0 313 515 | 9/1988 |
| JP | 59-166879 | 9/1984 |
| WO | WO 90/06357 | * 6/1990 |

OTHER PUBLICATIONS

Cox et al., "Isolation and characterization of milk growth factor, a transforming–growth–factor–β2–related polypeptide, from bovine milk", Eur. J. Biochem. 197:353–358 (1991).

Damerdji et al., "Utilization of Whey Fractions as a Substitute for Fetal Calf Serum in Culture Media", Biotech. Tech., vol. 2 No. 4, pp. 253–258 (1988).

Gaull et al., "Significance of Growth Modulators in Human Milk", Pediatrics, vol. 75 No. 1 Part 2, pp. 142–145 (Jan. 1985).

Klagsbrun, "Human milk stimulates DNA synthesis and cellular proliferation in cultured fibroblasts", Proc. Natl. Acad. Sci. USA, vol. 75 No. 10, pp. 5057–5061 (Oct. 1978).

Klagsbrun et al., The Serum–Free Growth of Balb/c 3T3 Cells in Medium Supplemented with Bovine Colostrum, Jour. of Supramolecular Structure, 11:349–359 (1979).

Koroly et al., "Nerve Growth Factor", Tissue Growth Factors, Chap. 8, pp. 249–276.

Oliver et al.,"A rapid and convenient assay for counting cells cultured in microwell plates: application for assessment of growth factors", Jour. of Cell Science, 92:513–518 (1989).

Yankner et al., "The Biology and Mechanism of Action of Nerve Growth Factor", Annual Review of Biochemistry, vol. 51, pp. 845–868.

Van Brunt et al., "Growth Factors Speed Would Healing", Biotechnology, vol. 6 No. 1 (Jan. 1988).

* cited by examiner

Primary Examiner—Jean C. Witz
(74) Attorney, Agent, or Firm—Merchant & Gould P.C.

(57) ABSTRACT

The invention relates to pharmaceutical or veterinary compositions for the treatment of surface wounds; pharmaceutical or veterinary compositions for the treatment of gastrointestinal injuries, diseases or ulcers; methods of treating surface wounds in animals, including humans; and methods for the treatment of gastrointestinal injuries, diseases or ulcers which compositions and methods include compositions of milk product extracts including growth factors with basic to approximately neutral isoelectric points.

3 Claims, 13 Drawing Sheets

(a) Loss of Mucosal Crypts (b) Loss of Mucosal Villi (a) Percentage (incidence) of rats showing bacterial translocation (b) Number of bacterial colonies per gram of intestinal lymph node

GROWTH-PROMOTING AGENT

CROSS-REFERENCE TO RELATED APPLICATIONS

The present application is a Divisional application of U.S. Ser. No. 09/082,987, filed May 22, 1998, U.S. Pat. No. 6,319,522 which is a Divisional application of U.S. Ser. No. 08/641,754, filed May 2, 1996, abandoned, and a Continuation-in-Part of U.S. Ser. No. 08/814,833, filed Mar. 11, 1997, abandoned, which are a Continuation-in-Part of U.S. Ser. No. 07/956,759, filed Dec. 7, 1992 U.S. Pat. No 5,866,418, application Ser. No. 07/956,759 was a national stage application based upon PCT/AU91/00303, filed Jul. 9, 1991. The parent application claims priority from Australian Provisional Patent Application PK 1170, filed Jul. 13, 1990. The present application also claims priority from Australian Provisional Patent Application PN 2712, which was filed May 2, 1995. Priority is claimed from the above-recited applications, to the extent entitled. The disclosures of the patent documents identified in this paragraph are specifically incorporated herein by reference.

FIELD OF THE INVENTION

This invention relates to the growth of animal cells in a cell culture composition. More specifically it relates to the provision of a cell culture composition including a milk product extract composition. This invention also relates to the growth of animal cells where that growth is associated with the repair of surface wounds or the repair of gastrointestinal injuries, diseases or ulcers, by the application of a composition including a milk product extract composition. This invention also relates to a method for preparing milk product extract composition.

BACKGROUND OF THE INVENTION

Animal cells are grown in culture to provide a number of pharmaceutical, diagnostic and veterinary products including human vaccines, lymphokines, hormones, monoclonal antibodies, other pharmaceutically active protein products, veterinary hormones and for research and development and diagnostic purposes.

The growth of animal cells requires a defined isotonic medium that contains salts, nutrients, lipid precursors, nucleic acid precursors, vitamins and amino acids that are formulated to mimic the medium that would normally bathe those cells in vivo. Examples in common use include Eagle's Minimal Essential Medium, Dulbecco's-modified Eagle's Minimal Essential Medium (DMEM), Medium 199, RPMI 1640 medium and Ham's F12 Medium. However, virtually no animal cells will grow in such a medium, but require the co-addition of serum. Fetal bovine serum is frequently used as it is more effective than serum obtained from postnatal animals and it contains only minimal concentrations of immunoglobulins which otherwise could have undesirable effects.

The supply of fetal bovine serum is limited by the number of pregnant cows slaughtered. It also has undesirable lot-to-lot variations and may include toxins. Particular concern surrounds its use for the eventual production of recombinant proteins and other pharmaceuticals for human use because the serum may also contain viruses that are harmful to humans and may be carried through a purification protocol that yields the desirable product. Principally for these reasons, extensive efforts have been directed towards the replacement of serum by pure ingredients. Examples of such ingredients are growth factors, hormones and cell attachment factors. Unfortunately, the requirements of each cell type being grown are different and are difficult to establish. Frequently it has not proved possible to achieve equivalent growth properties or equivalent yields of cell products with "serum-free" media as can be obtained with medium containing fetal bovine serum.

The limited availability of fetal bovine serum, its lot-to-lot variability, its resultant considerable cost as well as the deficiencies of "serum-free" media described above have prompted the investigation of other biological fluids as potential replacements in cell culture media. Some progress has been reported in the prior art with bovine milk and bovine colostrum as evidenced by the following selected reports: M. Klagsbrun: "Human milk stimulates DNA synthesis and cell proliferation in cultured fibroblasts" (Proc. Natl. Acad. Sci. USA 75, 5057, 1978); M. Klagsbrun & J. Neumann: "The serum-free growth of Balb/c 3T3 cells in medium supplemented with bovine colostrum" (J. Supramol. Struct. 11 349, 1979).

The prior art also includes U.S. Pat. No. 4,440,860 to M. Klagsbrun which describes "compositions and methods for promoting cell growth featuring, in one aspect, cell culture media containing milk or colostrum and fibronectin; fibronectin is preferably pre-coated onto the culture substrate" and Japanese Patent JP 59166879 to Morinaga "A culture medium for cell incubation—containing milk or milk components". Ultrafiltrates of milk whey have also been used to support the growth of cultured cells, as in O.Damerdji et al. Taken together, the prior art indicates that a range of cell growth stimulating factors are present in milk products, although a method for their isolation as a mixture to stimulate the growth of cultured cells that are separated from the major proteins in milk has not been described. "Utilization of whey fractions as a substitute for fetal calf serum in culture media" (Biotech. Tech. 2, 235, 1988).

The prior art also includes U.S. Pat. No. 5,077,276 "Growth Factor" to the applicants wherein the isolation of insulin-like growth factor IGF-I and des(1–3)IGF-I are described from bovine colostrum. A 25 kDa dimeric molecule, termed milk growth factor (MGF) has also been isolated from bovine milk by R. R. Burk et al. according to European Patent Application EP 0313515 and confirmed as transforming growth factor beta-2 (TGF-$\beta$2), (D. A. Cox and R. R. Burk, Eur. J. Biochem. 197, 353, 1991). The prior art also includes reports of epidermal growth factor (EGF) and platelet-derived growth factor (PDGF) in milk or colostrum (A. N. Corps. et al. J. Endocrinol. 112, 115, 1987).

Despite this progress a successful alternative to fetal bovine serum is yet to be located.

It is accordingly an object of the present invention to overcome, or at least alleviate one or more of the difficulties or deficiencies related to the prior art.

SUMMARY OF THE INVENTION

Accordingly in a first aspect of the present invention there is provided a milk product extract composition including a plurality of cell growth stimulating factors, extracted from milk product, in concentrated form; said factors having basic to approximately neutral isoelectric points.

The method for preparing the composition includes the steps of: providing a source of milk product, a cation-exchange resin, and a buffer solution; contacting the milk product with the cation-exchange resin such that the more basic components of the milk product are selectively adsorbed thereon; eluting the cation-exchange resin with the buffer solution to provide an eluate; and treating the eluate to remove salt therefrom.

The method can include additional steps such as treating the milk product sequentially by subjecting the milk product to a clarification step to remove insoluble materials therefrom; adjusting the pH of the clarified milk product to between approximately 6.5 and 8.0; contacting the clarified milk product with a cation-exchange resin; eluting from the cation exchange resin at high ionic strength or high pH with a suitable buffer solution to provide an eluate; and subjecting the eluate to a concentration step and diafiltration step to remove salt therefrom.

In the context of the invention, high pH refers to pH greater than about neutral pH, or about pH 7. Preferable high pH is greater than about pH 8, preferably more than about pH 9. In the context of the invention high ionic strength or high salt refers to a concentration as high as or higher than about 0.25 M, preferably at or above about 0.4 M, preferably at or above about 1 M. Recitation of high salt or high pH also includes high salt and high pH.

Another embodiment of the invention includes a milk product extract composition produced by a method of the invention. Certain milk product extract compositions of the invention are referred to as GFE, GFE-1, GFE-2, or GFE-3, and the like. GFE, or a like term, is generally synonymous with the term milk product extract composition. Typically GFE, or a like term, is used to refer to a specific, exemplified composition of the invention. GFE, or a like term, is also used to refer to one or more of a group of compositions that are produced by the same method but starting from different milk products. A milk product extract composition can also be referred to as a milk product extract.

One advantageous composition includes a plurality of cell growth stimulating factors extracted from a milk product in concentrated form. The factors in this advantageous composition have basic to approximately neutral isoelectric points. This advantageous composition is prepared by a method including: providing a source of milk product, a cation-exchange resin, and a buffer solution; contacting the milk product with the cation-exchange resin such that the more basic components of the milk product are selectively adsorbed thereon; eluting the cation-exchange resin with the buffer solution; and treating the eluate to remove salt therefrom.

A preferred milk product extract composition is prepared by treating a milk product sequentially by subjecting the milk product to a clarification step to remove insoluble materials therefrom and to provide a clarified milk product; adjusting the pH of the clarified milk product to between approximately 6.5 and 8.0; contacting the clarified milk product with a cation-exchange resin so that a plurality of cell growth stimulating factors present in the milk product are selectively adsorbed to the cation-exchange resin and wherein the major proteins with acidic isoelectric points in the milk product are not adsorbed; eluting from the cation-exchange resin at high ionic strength or high pH with a suitable buffer solution; and subjecting the eluate to a concentration step and diafiltration step to remove salt therefrom.

Accordingly in a further aspect of the present invention, there is provided a method for preparing a milk product extract composition including a plurality of cell growth stimulating factors, extracted from milk product in concentrated form; said factors having basic to approximately neutral-isoelectric points.

Although the method in particular applies to the growth of animal cells in vitro it can also be applied to animals, including humans, that have surface wounds. It has been found that a composition including a milk product extract according to the present invention can improve surface wound repair in vitro and in vivo.

Growth of (a) L6 myoblasts, (b) Balb C/3T3 fibroblasts and (c) SF1972 human skin fibroblasts in the presence of (●) fetal bovine serum (FBS), (○) GFE prepared according to Example 1 or (○) GFE-2 prepared according to Example 2. The details are described in Example 4.

FIG. 2

Growth promoting activities in human umbilical vein endothelial cells in the presence of cheese whey extract (GFE-2, Example 2). Data are expressed as the percentage $^3$H-thymidine incorporation above control cultures grown in serum-free medium only. The details are given in Example 7.

FIG. 3

Contraction of a fibroblast-populated collagen gel in response to cheese whey extract (GFE-2, Example 2). Fibroblast-induced contraction of the gel was assessed by counting the radioactivity remaining in the gel after 24 h culture (mean±SEM of triplicate determinations). The details are given in Example 8.

FIG. 4

Excisional wound closure in organ-cultured fetal rat skin in response to (●) FBS, (○) DMEM and (▲) cheese whey extract (GFE-2, Example 2). Wound repair was assessed by recording the ability of the cheese whey extract at the indicated concentrations to promote repair of the excisional deficit over a 72 h period. Other details are given in Example 9.

FIG. 5

Strength of incisional wounds in normal rats after single dose treatment with either (●) a vehicle preparation (rat tail collagen at 1 mg/ml) or (■) vehicle plus cheese whey extract (GFE-2, Example 2). Data are plotted as wound breaking strength (g) against time. Other details are given in Example 10.

FIG. 6

Figure 6:
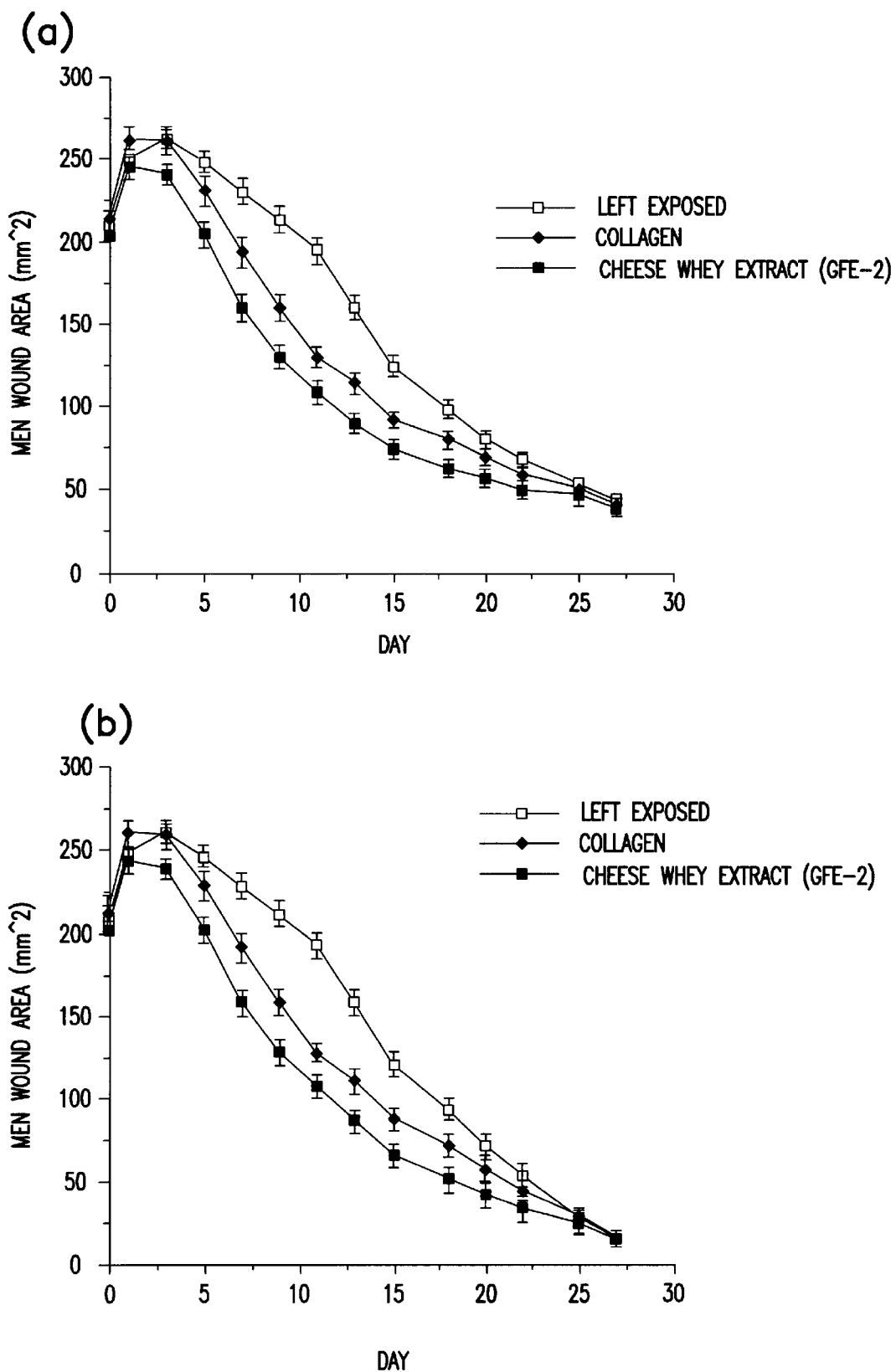
Figure 7:
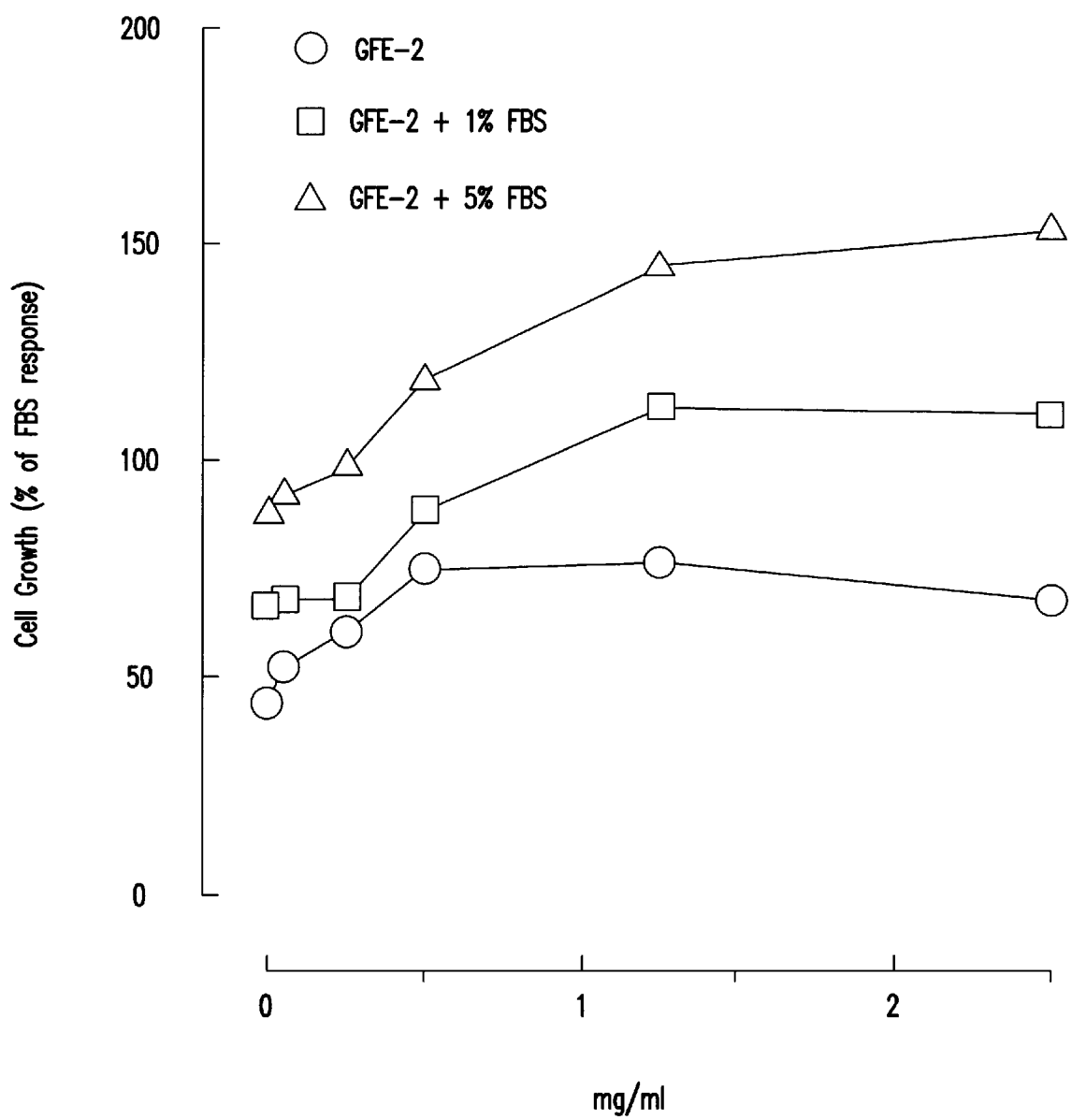

Contraction and epithelialization of excisional wounds on steroid-treated rats after treatment with either (■) cheese whey extract (GFE-2, Example 2) or (♦) collagen vehicle alone, compared to wounds that were (□) untreated and left exposed. Wounds were treated with either vehicle preparation (1 mg/ml collagen) or vehicle plus cheese whey extract (2.5 mg/ml) daily for 10 days after wounding. A further group of control wounds received no treatment and were left exposed. Wound repair was measured by tracing both the full thickness wound margin and epithelial margin onto transparent sheets at various time points after wounding. FIG. 6(a) shows full thickness wound area ($MM^2$) vs time as a measure of wound contraction. FIG. 6(b) incorporates the epithelial component of excisional wound repair. Other details are given in Example 11.

FIG. 7

Growth promoting activities of cheese whey extract (GFE-2, Example 2) on IEC-6 (rat intestinal epithelial) cells. GFE-2 was added either (○) alone or in the presence of (□) 1% FBS or (Δ) 5% FBS. Cell growth is expressed as a percentage of that obtained in the presence of 10% FBS. Other details are given in Example 12.

FIG. 8

Oral administration of cheese whey extract (GFE-2, Example 2) for 5 days to methotrexate-injected rats reduces small intestinal damage as assessed by (a) loss of mucosal crypt area (b) loss of mucosal villi area. Means±SEM, N=8. Other details are given in Example 13.

FIG. 9

Oral administration of cheese whey extract (GFE-2, Example 2) for 5 days to methotrexate-injected rats increases sucrose activity in the ileum. Means±SEM, N=8. Other details are given in Example 14.

FIG. 10

Oral administration of cheese whey extract (GFE-2, Example 2) for up to 12 days to methotrexate-injected rats reduces bacterial translocation across the gut.

(a) Percentage of rats showing bacterial translocation, (b) Number of bacterial colonies per gram of intestinal lymph node. Means±SEM, N=8. Other details are given in Example 15.

FIG. 11

Daily treatment of the cheek pouch in hamsters with a milk product extract (GFE-2) reduces the severity of oral mucositis ulcers caused by -5-fluorouracil;

FIG. 12

Daily treatment of the cheek pouch in hamster with a milk product extract (GFE-2) reduces the body weight loss induced by 5-fluorouracil.

FIG. 13

Electrophoretogram of proteins in cheese whey and the proteins that were separated by Sepharose Fast Flow S cation-exchange chromatography. Lane 1 shows molecular weight standards; lane 2 shows cheese whey; lane 3 is the first eluate; lane 4 is the second eluate; lane 5 is the first "flow through"; lane 6 is the second "flow through". Additional details are given in Example 4.

DETAILED DESCRIPTION

By the term "milk product extract" we mean an extract from human or animal milk product in which the salt and/or main protein constituents thereof are reduced or eliminated. Examples of milk product extracts include cheese whey extracts, skim milk extract and acid (casein) whey extract, and extracts of colostrum. Milk products of the invention include cheese whey, skim milk, acid (casein) whey, and colostrum.

The range of isoelectric points described by the term "basic to approximately neutral isoelectric point" includes isoelectric points between about 6.0 and about 10.5 or between approximately 6.0 and approximately 10.5, preferably between 6.0 and about 10.5, preferably between 6.0 and approximately 10.5.

The present invention will be more fully described with reference to the preferred cheese whey extracts. However, this is illustrative only and should not be taken as a restriction on the generality of the invention.

Preferably the milk product extract composition is a cheese whey extract composition.

The cheese whey extract composition may be formed from cheese whey wherein the salt and/or main protein constituents thereof are reduced or eliminated.

The milk product extract composition may include reduced amounts of alpha lactalbumin; beta lactoglobulin and casein compared with said milk product. Preferably, the milk product extract includes less than approximately 1% w/w of the salt present in the original milk product. The milk product extract may include less than approximately 0.5% of the casein, alpha lactalbumin, beta lactoglobulin, immunoglobulin and/or albumin present in the original milk product.

The milk product extract composition according to this aspect of the present invention may be utilized in the promotion of cell growth and proliferation in vitro as discussed below. The milk product extract composition may be utilized in stimulation of surface wound repair in vivo, or for the treatment of gastrointestinal injuries, diseases or ulcers, in mammals as discussed below.

Surprisingly, the milk product extract composition may support the growth of animal cells at lower protein concentrations than achieved with fetal bovine serum, yet with an efficacy comparable to fetal bovine serum for several cell types.

Alternatively, the milk product extract may be used as a supplement to media containing low concentrations of fetal bovine serum in order to achieve better growth rates of cultured cells and to conserve the use of fetal bovine serum.

Cheese whey is a by-product of the cheese industry that has had essentially all the fat and casein removed during cheese manufacture. At the present state of the art cheese whey is essentially valueless, and indeed it may represent a net cost to the industry since it is a potential pollutant.

Cheese whey for example is a low protein, high salt product available in tonne amounts from cheese manufacture. The main protein constituents present in cheese whey are alpha lactalbumin ($\alpha$LA) and beta lactoglobulin ($\beta$LG), which usually account for more than 90% of the proteins present. Significant amounts of serum albumin, immunoglobulins and residual casein may be present. All of these proteins have acidic isoelectric points. In contrast, the main protein factors that stimulate the growth of animal cells have basic isoelectric points. Examples include the growth factors basic FGF, IGF-I, des(1–3) IGF-I and PDGF. It is postulated that the extraction of the basic factors present in milk products such as cheese whey in the virtual absence of the otherwise abundant acidic proteins may account for the surprising efficacy of the milk product extract composition.

Accordingly in a further aspect of the present invention, there is provided a method for preparing a milk product extract composition including a plurality of cell growth stimulating factors, extracted from milk product in concentrated form; said factors having basic to approximately neutral isoelectric points, which method includes providing
   source of milk product;
   cationic exchange resin; and
   buffer solution;
contacting the milk product with the cation exchange resin such that the more basic components of the milk product are absorbed thereon;
eluting the cationic exchange resin with the buffer solution; and filtering the eluate to remove salt therefrom.

The term "selectively" is used to describe a process whereby the more basic components of the milk product are selectively adsorbed to a cation exchange resin whereas the acidic components are not. For example, few of or only a small portion of the acid components are bound to the resin, but many of or a substantial portion of the basic components are adsorbed. Typically the cation exchange resin is selected to selectively adsorb a plurality of a cell growth stimulating factors present in the milk product and major proteins with acid isoelectric points in the milk product are not adsorbed.

The desorption of the basic proteins from the ion exchange resin leads to a preparation enriched in cell growth stimulating factors. The eluate may be concentrated and filtered utilizing any suitable technique. The eluate may be concentrated for example by conventional ultrafiltration methods or other procedures to yield a mixture of proteins which supports the growth of animal cells when added to protein-free media such as DMEM.

The source of milk product may be a milk product filtrate substantially free of insoluble material. Milk products of the invention include cheese whey, skim milk, acid (casein) whey, and colostrum. Skim milk typically has higher protein and fat concentrations and lower salt concentrations than cheese whey. Skim milk also contains higher amounts of insoluble protein, especially particulate casein. In order to obtain a suitable milk product extract composition from skim milk, a filtration step before contacting the skim milk with the cation-exchange resin is typically required unless the selected cation-exchange resin has flow and adsorption characteristics that make it suitable for use with fat-containing and particulate-containing fluids.

Colostrum is the fluid produced during the first few days of lactation. Colostrum has a much higher protein concentration than skim milk or cheese whey and is well known in the art to contain cell growth stimulating factors. The higher protein concentration of colostrum could facilitate the isolation of cell growth stimulating factors because much smaller volumes can need to be applied to the cation-exchange resin. However, colostrum has a high fat content and in many mammalian species contains high concentrations of immunoglobulins. These two aspects make it technically more difficult to isolate cell growth stimulating factors on a large scale because, firstly, the preliminary filtration step in the process will need to be particularly efficient, and secondly, proportionally more cation-exchange resin can be required because immunoglobulins can be adsorbed to the resin.

Accordingly the preparation method may include the preliminary step of filtering the milk product to remove insoluble materials therefrom.

The milk product may be clarified by centrifugation or filtration, such as by filtration through a suitable sieve. The milk product may be filtered through a hollow fiber cartridge of defined porosity.

The cationic exchange resin may be of any suitable type provided that the plurality of cell growth stimulating factors present in the milk product are adsorbed to the cation-exchange resin and wherein the major proteins with acidic isoelectric points in the milk are not adsorbed, after which the cell growth stimulating factors can be eluted.

The suitability of a cation-exchange resin can be evaluated by passing a milk product through a column of the resin to be tested at neutral pH, or at another defined pH that is advantageous for the adsorption or separation, and measuring the proportion of growth factors in the milk product that are adsorbed and hence removed from the milk product, or separated from the eluate. The test adsorption of IGF-I, PDGF, basic FGF and TGF-β is typically particularly useful because these growth factors have convenient assays available in the prior art and a mixture containing them provides a good indicator of the plurality of growth stimulating factors of the present invention.

As well as testing cation-exchange resins for their abilities to adsorb the plurality of growth stimulating factors present in a milk product, the cation-exchange resin of choice must not adsorb significant proportions of the major acidic proteins in the milk product. This second property of the present invention can be readily evaluated by comparing the protein constituents of the milk product with the protein constituents of the fluid after it has passed through a column of the cation-exchange resin under test. Many chromatographic and electrophoretic methods are present in the prior art which are suitable for this purpose. Electrophoresis using the Pharmacia Phast gel system is particularly useful as the two most abundant acidic proteins, alpha lactalbumin and beta lactoglobulin, are well separated from the minor constituents of basic proteins, lactoperoxidase and lactoferrin. Thus a cation-exchange resin that adsorbs lactoperoxidase and lactoferrin but does no adsorb significant amounts of alpha lactalbumin or beta lactoglobulin is a good indicator for a suitable resin. This property, together with the property of the resin to adsorb IGF-I, PDGF, basic FGF and TGF-β will indicate the suitability of a cation-exchange resin under test.

Other properties of a cation-exchange resin such as flow characteristics, ability to function effectively in the presence of fats, total capacity of the resin and convenience of elution properties are likewise important in the selection of a suitable cation exchange resin.

A Sepharose-based cation exchange gel may be used. Sepharose is a trade name for a family of agarose-based cation exchangers. Agarose-based cation exchangers are but one member of a group of, and are representative of, weakly acidic cation exchangers that are suitable for purification of proteins, such as the mixture of milk proteins described herein. The contacting step may be conducted at neutral to basic pH, provided that the conditions are selected so that a plurality of cell growth stimulating factors present in the milk product are selectively adsorbed to the cation-exchange resin and wherein the major proteins with acidic isoelectric points in the milk product are not adsorbed. The contacting step may be conducted at a pH of approximately 6.5 to 8.0.

The cationic exchange resin may be equilibrated with a suitable buffer at a pH of approximately 6.5 to 8.0. An aqueous sodium citrate buffer may be used. The elution steps may be conducted utilizing a suitable eluate. A salt solution may be used. A buffered saline solution may be used.

Thus in a preferred form of this aspect of the present invention the method of preparing a milk product extract composition may include treating milk product sequentially by:

subjecting the milk product to a filtration step, to remove insoluble materials therefrom;

adjusting the pH of the filtrate to between approximately 6.5 and 8.0;

contacting the filtrate with a cationic exchange resin so that a plurality of cell growth stimulating factors present in the milk product are selectively adsorbed to the cation-exchange resin and wherein the major proteins with acidic isoelectric points in the milk product are not adsorbed;

eluting from the cation exchange resin at high ionic strength and high pH with a suitable buffer solution; and subjecting the eluate to a concentration step and diafiltration step to remove salt therefrom.

Preferably the milk product is clarified by filtration to remove insoluble materials therefrom and to provide a filtrate which is substantially free of insoluble materials. The pH of the filtrate is preferably adjusted to between approximately 6.5 to 8.0 or between about 6.5 and about 8.

Alternatively, the elution from the cation exchange resin is achieved at high ionic strength but without adjusting pH, such that the cell growth stimulating factors are recovered. For example, the cell growth stimulating factors adsorbed to a Sepharose-based cation-exchange resin can be eluted with 0.4M NaCl at pH 6.5. Advantageously elution from the cation exchange resin is conducted without adjusting pH and cell growth stimulating factors are recovered.

In this embodiment the cell growth stimulating factors are eluted with less extraneous protein.

In another preferred aspect of the present invention, the diafiltration step used to remove salt from the eluate can include a diafiltration against 150 mM NaCl or a volatile salt, for example, ammonium bicarbonate. The 150 mM NaCl provides an isotonic solution suitable for filter sterilization and use in cell culture. In a preferred embodiment, filter sterilization follows the diafiltration step.

In a preferred form of this aspect of the present invention the method of preparing a milk product extract composition can further include treating a milk product sequentially by:
  subjecting the milk product to a clarification step, to remove insoluble materials therefrom to provide a clarified milk product;
  adjusting the pH of the clarified milk product to between approximately 6.5 and 8.0 or between about 6.5 and about 8;
  contacting the clarified milk product with a cation exchange resin so that a plurality of cell growth stimulating factors present in the milk product are selectively adsorbed to the cation-exchange resin and wherein major proteins with acidic isoelectric points in the milk product are not adsorbed;
  eluting from the cation-exchange resin at high ionic strength but without adjusting pH, such that the cell growth stimulating factors are recovered;
  subjecting the eluate to a concentration step and diafiltration step against 0.15 M NaCl; and
  filter sterilization of the isotonic filtrate.

In another preferred aspect of the present invention, the diafiltration step used to remove salt or adjust the salt to 0.15 M NaCl can be replaced by diafiltration against a volatile salt. Ammonium bicarbonate is particularly suitable for this purpose. Use of a volatile salt is particularly useful if the eluate is to be freeze dried or spray dried as the volatile salt is removed by such a process.

Thus in a preferred form of this aspect of the present invention the method of preparing a milk product extract composition can include treating milk product sequentially by:
  subjecting the milk product to a clarification step, to remove insoluble material therefrom to provide a clarified milk product;
  adjusting the pH of the clarified milk product to between approximately 6.5 and 8.0 or between about 6.5 and about 8;
  contacting the clarified milk product with a cation-exchange resin so that a plurality of cell growth stimulating factors present in the milk product are selectively adsorbed to the cation-exchange resin, and wherein the major proteins with acidic isoelectric points in the milk product are not adsorbed;
  eluting from the cation-exchange resin at high ionic strength but without adjusting pH, such that the cell growth stimulating factors are recovered;
  subjecting the eluate to a concentration step and diafiltration step against a solution of a volatile salt; and
  subjecting the diafiltered eluate to a freeze drying process or spray drying process.

Optionally the diafiltered eluate can be filter sterilized before the freeze drying process or spray drying process. The milk product extract composition of the present invention can be isolated from milk products other than cheese whey provided that the method is modified appropriately. Under certain commercial conditions skim milk or colostrum can be attractive as starting milk products.

In a further aspect of the isolation of a suitable extract from cheese whey, the eluant may be treated at high temperature and centrifuged. This modification removes additional protein. Accordingly, the method may further include subjecting the eluant to a heat treatment to reduce the content of extraneous protein. Such a step can be included in a method that also includes filter sterilization of the eluate prior to a freeze drying process or spray drying process.

The milk product extract composition may be sterilized and optionally freeze-dried for storage. The freeze-dried material may be dissolved in sterile saline for addition to cells in culture.

Accordingly the present invention includes a milk product extract composition including a plurality of cell growth stimulating factors, extracted from a milk product in concentrated form; said factors having basic to approximately neutral isoelectric points, which method includes
  providing
    a source of milk product;
    a cation-exchange resin; and
    a buffer solution;
  contacting the milk product with the cation-exchange resin such that the more basic components of the milk product are selectively absorbed thereon;
  eluting the cation-exchange resin with the buffer solution; and
  treating the eluate to remove salt therefrom.

There is also provided a milk product extract composition prepared by treating a milk product sequentially by:
  subjecting the milk product to a clarification step, to remove insoluble materials therefrom to provide a clarified milk product;
  adjusting the pH of the clarified milk product to between approximately 6.5 and 8.0 or between about 6.5 and about 8;
  contacting the clarified milk product with a cation-exchange resin so that a plurality of cell growth stimulating factors present in the milk product are selectively adsorbed to the cation-exchange resin and wherein the major proteins with acidic isoelectric points in the milk product are not adsorbed;
  eluting from the cation-exchange resin at high ionic strength or high pH with a suitable buffer solution; and
  subjecting the eluate to a concentration step and diafiltration step to remove salt therefrom.

In a further aspect of the present invention there is provided a cell culture composition including an effective amount of a milk product extract composition including a plurality of cell growth stimulating factors, extracted from milk product, in concentrated form; said factors having basic to approximately neutral isoelectric points; and
  a culture medium.

The culture medium may be a substantially protein-free isotonic culture medium. The substantially protein-free isotonic culture medium may be Dulbecco's-Modified Eagle's Minimal Essential Medium (DMEM).

It has been found that an approximately equivalent growth rate of human skin fibroblasts to that achieved with 5% Fetal Bovine Serum may be achieved with approximately 20 μg of cell growth stimulating factors extracted from cheese whey according to the preferred aspect of the present invention per 100 μl of medium.

Alternatively a small but effective amount of fetal bovine serum may be utilized as the culture medium. It has been found that the addition of approximately 25 μg of cell growth stimulating factors per 100 μg of medium containing approximately 2% fetal bovine serum will increase the growth rate of Balb C/3T3 cells to that rate otherwise achieved with 10% fetal bovine serum.

Other additions may be made to the medium, depending on the cell type, including growth factors, attachment factors or low amounts of serum.

In a preferred form, the present invention provides a cell culture composition, as described above, wherein the milk product extract is present in media at a protein concentration of approximately 10 to 20,000 micrograms per ml, preferably 100 to 2,000 micrograms per ml.

Accordingly in a still further aspect of the present invention there is provided a method for culturing cells which method includes
 providing
  source of animal cells; and
  a cell culture composition including an effective amount of a milk product extract composition including
  a plurality of cell growth stimulating factors, extracted from milk product, in concentrated form; said factors having basic to approximately neutral isoelectric points; and
  a substantially protein-free isotonic culture medium; and
 culturing the cells in the cell culture composition for a time sufficient, and at a temperature sufficient to achieve a predetermined cell concentration.

The cell culture method may be conducted at ambient temperature or above. A temperature in the range of approximately 35 to 40° C. may be used.

The cell culture process may be conducted in an incubator, for example a humidified incubator.

The cell culture method may be conducted on any suitable surface or in suspension. Tissue culture plates may be used.

The cell culture method may continue for a period of approximately 1 to 5 days depending on the cell concentration desired.

The composition of the present invention has been shown to contain a number of growth stimulating factors including IGF-I, IGF-II, PDGF, TGF-β and basic FGF. However, when these factors are added to cell culture media, either individually at optimal concentrations, or together at the respective proportions present in the milk product extract, they are unable to stimulate the growth of cells as effectively as the milk product extract. In other words, the composition of the present invention provides an advantageous combination of known and unknown growth stimulating factors that are prepared by a simple method. Both the increased stimulation of growth compared to known growth factors, either alone or in combination, and ease of preparation are among the advantageous features of the present compositions and methods. These findings indicate the presence of unknown cell growth stimulating factors in the milk product extract and indicate the particular advantages of the present invention.

The prior art includes the isolation and characterization of TGF-β2 from bovine milk, and the prior art in some cases refers to TGF-β2 as a growth factor termed "milk growth factor" (D. A. Cox and R. R. Burk, Eur. J. Biochem. 197, 353, 1991; European Patent Application 0313 515). This factor in pure form or partially purified from milk product is shown to stimulate the growth of certain cell types but inhibits the growth of others whose growth is stimulated by the growth stimulating factors of the present invention. Hence TGF-β2 cannot account for the growth stimulating properties of the present invention.

Although the method in particular applies to the growth of animal cells in vitro it can also be applied to animals, including humans, that have surface wounds.

It has been found that a composition including a milk product extract according to the present invention can improve surface wound repair in vitro and in vivo.

As used herein, the term "surface wounds" includes the following types of damage:
 (a) ulcers of all kinds including pressure ulcers such as pressure sores, bed sores or decubitis ulcers, as well as ulcers associated with vascular disease such as venous ulcers, varicose ulcers, and ulcers associated with diabetes, autoimmune disease, sickle cell diseases or hemophilia;
 (b) conditions that result from surgery such as debridement, skin grafting, partial thickness wounds that result after removal of skin for grafting, and full thickness incisions;
 (c) therapeutically induced wounds including those induced during radiotherapy or in response to drugs;
 (d) wounds associated with disorders of the central nervous system that may alter sensation or affect mobility;
 (e) wounds that result from any exfoliative disease of the skin;
 (f) wounds associated with either local or systemic infection such as yaws or
 (g) congenital wounds such as spina bifida;
 (h) pathological wounds that include wounds associated with skin cancers;
 (i) traumatic and accidental wounds including penetrations, lacerations, abrasions, gouges and other trauma, and
 (j) burns.

Accordingly, in a further aspect, the present invention provides a pharmaceutical or veterinary composition for the treatment of surface wounds, which composition includes:
 an effective amount of a milk product extract composition including a plurality of cell growth promoting factors, extracted from milk product in concentrated form; said factors having basic to approximately neutral isoelectric points; and
 a pharmaceutically or veterinarily acceptable diluent, carrier or excipient therefor.

In a particularly preferred form, the present invention provides a pharmaceutical or veterinary composition for the treatment of surface wounds which composition includes:
 (a) a milk product extract that contains a mixture of cell growth factors with basic to approximately neutral isoelectric points, preferably isoelectric points between about 6.0 and about 10.5, preferably isoelectric points between 6.0 and about 10.5. The mixture of cell growth factors can be obtained from a milk product of an ungulate mammal by first subjecting that product to a cation exchange matrix under conditions whereby casein, alpha lactalbumin, and beta lactoglobulin present in the milk product are not absorbed to the matrix, after which the absorbed growth factor mixture is eluted and then concentrated; and (b) a pharmaceutically or veterinarily acceptable diluent, carrier or excipient therefor.

The pharmaceutical or veterinary composition may further include an effective amount of at least one active ingredient.

The at least one active ingredient may be selected from antibiotics, antiseptics, other growth promotants, anaesthetics, and the like, and mixtures thereof.

The pharmaceutical or veterinary composition may be adapted for administration in any suitable manner. The composition may be adapted for internal or topical administration. The composition may be in an oral, injectable or topical form. Topical administration is preferred. The composition may take the form of a wash, lotion, cream, ointment or gel.

There are no limitations to the type of surface wound that may be treated, and these include, but are not limited to ulcers, conditions that result from surgery, therapeutically induced wounds, wounds associated with disorders of the central nervous system, any exfoliative disease of the skin, wounds associated with local or systemic infection, congenital wounds, pathological wounds, traumatic and accidental wounds, and burns.

Accordingly, in a further aspect of the present invention there is provided a method of treating surface wounds in animals, including humans, which method includes administering to a subject to be treated an effective amount of a pharmaceutical or veterinary composition, which composition includes an effective amount of a milk product extract composition including a plurality of cell growth promoting factors, extracted from milk product in concentrated form; said factors having basic to approximately neutral isoelectric points; and a pharmaceutically or veterinarily acceptable diluent, carrier or excipient therefor.

In a particularly preferred form, the present invention provides a method of treating surface wounds in animals, including humans, which method includes administering to a subject to be treated an effective amount of a pharmaceutical or veterinary composition, which composition includes:

(a) a milk product extract that contains a mixture of cell growth factors with basic to approximately neutral isoelectric points, preferably isoelectric points between about 6.0 and about 10.5, preferably isoelectric points between 6.0 and about 10.5. The mixture of cell growth factors can be obtained from a milk product of an ungulate mammal by first subjecting that product to a cation exchange matrix under conditions whereby casein, alpha lactalbumin, and beta lactoglobulin present in the milk product are not absorbed to the matrix, after which the absorbed growth factor mixture is eluted and then concentrated; and (b) a pharmaceutically or veterinarily acceptable diluent, carrier or excipient therefor.

In the above method, the milk product extract may be applied directly to wounds in a biologically acceptable carrier to ensure sustained release at sufficient concentration in the wound environment. Such carriers include any synthetic or biological polymer, glycosaminoglycan, or extracellular matrix molecule (eg. fibrin, collagen, gelatin, synthetic polymers, agarose, alginates, methylcellulose, hyaluronic acid, hydrocolloids, alginates). The carrier may be in the form of a gel. Alternatively the milk product extract could be administered in the form of a spray (in a biologically acceptable diluent, for example a buffer solution), powder, ointment, salve or irrigant or incorporated or impregnated into a dressing (absorbable and non-absorbable), transdermal patches or releasably associated with gauze, bandages, sutures, plasters, staples, prosthetic devices, screws or plates (biodegradable or non-biodegradable). Alternatively, the milk product extract may be incorporated into a toothpaste, gum or resin for chewing or provided as a mouth wash.

In another aspect the present invention relates to a wound support including an effective amount of a milk product extract composition including a plurality of cell growth promoting factors, extracted from milk product in concentrated form; said factors having basic to approximately neutral isoelectric points.

As used herein the term "wound support" includes any means which is used to support or secure a wound and includes a surgical securing means. The term includes plasters, dressings, sutures, staples and the like. The wound to be supported may be a wound created by surgery, or the result of accident or other injury. The milk product extract may be present on the surface of the wound support or may be impregnated in the wound support and is able to be released therefrom.

The milk product extract may have other molecules associated therewith to aid releasability, stability, solubility, activity and/or association with the wound support, including adjuvants, carriers, solubilizing agents, and growth factors. Furthermore, the milk product extract may be used in combination with other compounds or molecules which act in synergistic, agonistic and/or additive concert. There are no limitations to the nature of these ingredients except they should be pharmacologically and physiologically acceptable for administration and should not degrade the activity, or render harmfully toxic the active ingredients.

Preferably the milk product extract when used in the above described methods is administered in an amount from 0.01 to 10 mg/ml of fluid in the local environment at the wound side. The milk product extract may be delivered during the peri or post operative period. Alternatively the milk product extract may be impregnated or present on the surface of an adhesive dressing, occlusive plaster or surgical securing means such as sutures or staples.

It will be understood by those skilled in the art that the milk product extract may be administered for a time and under conditions sufficient to allow for wound repair.

The composition of the present invention may also be used to treat animals, including humans, that have gastrointestinal injuries, diseases or ulcers. It has also been found to improve the growth rate of gastrointestinal cells in vitro.

As used herein the term "gastrointestinal injuries, diseases or ulcers" includes the following types of damage to or diseases of the gastrointestinal tract:

(a) dental and oral wounds, including those associated with periodontal disease;

(b) peptic ulceration of the duodenum, stomach or esophagus;

(c) inflammatory bowel diseases such as ulcerative colitis or Crohn's disease;

(d) ulcers associated with stress conditions, for example burns, trauma, sepsis, shock, intracranial surgery or head surgery;

(e) damage to the lining of the alimentary tract resulting from radiotherapy and/or chemotherapy with agents such as mechlorethamine, melphalan, busulphan, cytarabine, floxuridine, 5-fluorouracil, mercaptopurine, methotrexate, thioguanine, bleomycin, actinomycin-D, daunorubicin, etoposide, mitomycin, vinblastine, vincristine, hydroxyurea or procarbazine;

(f) inadequate gut function or damage to the gut associated with prematurity such as narcotizing enterocolitis or poor gut motility;

(g) diarrheal conditions such as associated with bacterial, viral, fungal or protozoan infection, including AIDS;

(h) food intolerances such as coeliac disease;

(i) cancers of the gastrointestinal tract, including buccal cavity, esophagus, stomach or bowel;

(j) surgically induced damage such as following partial gut resection, short gut syndrome, jejunostomy, ileostomy, colostomy;

(k) damage due to esophageal reflux;

(l) conditions associated with loss of gut barrier function such as external burns, trauma, sepsis or shock;

(m) congenital conditions resulting in inadequate gastrointestinal function or damage such as volvulus and cystic fibrosis; and (n) autoimmune diseases that affect the gut, such as Sjogren's Syndrome.

Accordingly, in a further aspect, the present invention provides a pharmaceutical or veterinary composition for the treatment of gastrointestinal injuries, diseases or ulcers, which composition includes:

an effective amount of a milk product extract composition including a plurality of cell growth promoting factors, extracted from milk product in concentrated form; said factors having basic to approximately neutral isoelectric points; and a pharmaceutically or veterinarily-acceptable diluent, carrier or excipient therefor.

In a particularly preferred form, the present invention provides a pharmaceutical or veterinary composition for the treatment of gastrointestinal injuries, diseases or ulcers which composition includes:

(a) a milk product extract that contains a mixture of cell growth factors with basic to approximately neutral isoelectric points, preferably isoelectric points between about 6.0 and about 10.5, preferably isoelectric points between 6.0 and about 10.5. The mixture of cell growth factors can be obtained from a milk product of an ungulate mammal by first subjecting that product to a cation exchange matrix under conditions whereby casein, alpha lactalbumin, and beta lactoglobulin present in the milk product are not absorbed to the matrix, after which the absorbed growth factor mixture is eluted and then concentrated; and (b) a pharmaceutically or veterinarily acceptable diluent, carrier or excipient therefor.

There are no limitations to the type of gastrointestinal injuries, diseases or ulcers that may be treated, and these include, but are not limited to dental and oral wounds, peptic ulcers, inflammatory bowel diseases, ulcers associated with stress conditions, damage caused by radiotherapy and/or chemotherapy, inadequate gut function or damage associated with prematurity, diarrheal conditions, damage caused by food intolerance, cancer of the gastrointestinal tract, surgically induced damage, damage caused by esophageal reflux, conditions associated with loss of gut barrier function, congenital conditions resulting in inadequate gastrointestinal function or damage, and autoimmune diseases that affect the gut.

Accordingly, in a still further aspect of the present invention, there is provided a method for the treatment of gastrointestinal injuries, diseases or ulcers, which method includes administering to a subject to be treated an effective amount of a pharmaceutical or veterinary composition, which composition includes an effective amount of a milk product extract composition including cell growth promoting factors, extracted from milk product in concentrated form and having a basic to approximately neutral isoelectric point; and a pharmaceutically or veterinarily acceptable diluent, carrier or excipient therefor.

In a particularly preferred form, the present invention provides a method for the treatment of gastrointestinal injuries, diseases or ulcers, which method includes administering to subject to be treated an effective amount of a pharmaceutical or veterinary composition, which composition includes:

(a) a milk product extract that contains a mixture of cell growth factors with basic to approximately neutral isoelectric points, preferably isoelectric points between about 6.0 and about 10.5, preferably isoelectric points between 6.0 and about 10.5. The mixture of cell growth factors can be obtained from a milk product of an ungulate mammal by first subjecting that product to a cation exchange matrix under conditions whereby casein, alpha lactalbumin, and beta lactoglobulin present in the milk product are not absorbed to the matrix, after which the absorbed growth factor mixture is eluted and then concentrated; and (b) a pharmaceutically or veterinarily acceptable diluent, carrier or excipient therefor.

In the above method the milk product extract may be administered directly into the alimentary canal by oral delivery or other means of direct enteral administration, in order to maximize the effective dose reaching the affected tissue.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; as a mouthwash or as an oil-in-water liquid emulsion or a water-in-oil liquid emulsion. The active ingredient may also be presented as a bolus, electuary or paste.

Compositions suitable for parenteral administration include aqueous and non-aqueous sterile injection solutions which may contain anti-oxidants, buffers, bacteriostats and solutes; and aqueous and non-aqueous sterile suspensions which may include suspending agents and thickening agents. The compositions may be presented in unit-dose or multidose sealed containers, for example, ampoules and vials, and may be stored in a freeze-dried condition requiring only the addition of the sterile liquid carrier, for example water for injections, immediately prior to use. Solutions and suspensions may be prepared from sterile powders, granules and tablets of the kind previously described.

It should be understood that in addition to the ingredients particularly mentioned above, the compositions of this invention may include other agents conventional in the art having regard to the type of composition in question, for example, those suitable for oral administration may include such further agents as sweeteners, thickeners and flavoring agents.

The milk product extract may be administered at any appropriate time including prior to, during or after the gastrointestinal injuries, diseases or ulcers have become evident.

The milk product extract may be useful in combination with known therapeutic agents. If formulated as a fixed dose, such combination products may employ the milk product extract in an appropriate dosage range and the other pharmaceutically active agent within its approved dosage range. Compositions of the invention may be used sequentially with known therapeutic agents when a combination formulation is inappropriate.

When the milk product extract is administered to a human subject the daily dosage can be determined by the attending physician with the dosage generally varying according to the age, weight, and response of the individual patient, as well as the severity of the patient's symptoms. In general a suitable dose of the milk product extract of the invention will be in the range of 20 mg to 20 g per kilogram body weight of the recipient per day, preferably in the range of 200 mg to 2 g per kilogram body weight per day. However, the dose will also depend on the formulation and purity of the milk product extract used. The above mentioned doses are calculated on the basis of the cheese whey product extract described in Example 2 and could be modified accordingly by a person skilled in the art if a product of different activity or purity was used.

The present invention will now be more fully described with respect to the following examples. It should be understood, however, that the description following is illustrative only, and should not be taken in any way as a restriction on the generality of the invention described above.

As examples of wound repair in vitro, the cheese whey extract promotes the growth of human skin fibroblasts and human endothelial cells, cell types that are major components of the skin.

In a further example of wound repair in vitro, the cheese whey extract stimulates the contraction of a fibroblast-populated collagen gel, a process that is analogous to the desired contraction of a wound in vivo.

In yet a further example of wound repair in vitro, the cheese whey extract induces the closure of a full thickness excisional wound in cultured fetal rat skin.

As an example of wound repair in vivo, it was found that the cheese whey extract enhanced the strength of an incisional wound in normal rats at 5 days or 7 days after a single treatment.

In a second example of wound repair in vivo, it was found that full thickness, excisional wounds on steroid-compromised rats repaired more rapidly when treated daily with the cheese whey extract than with the vehicle solution. In this example both wound contraction and wound epithelialization were improved by the treatment.

It has also been found that the cheese whey extract when administered to rats at the same time as the chemotherapy agent methotrexate can reduce the loss of mucosal crypts and villi in the jejunum and ileum regions of the gut. The treatment protocol can also lead to an increase in the activity of the digestive enzyme, sucrase, above that in animals that only receive methotrexate.

In a second investigation on rats having their gut damaged with methotrexate, the incidence of bacterial translocation across the gut is reduced at 9 and 12 days after treatment with the cheese whey extract. Moreover, the number of bacterial colonies detected in intestinal lymph nodes is reduced at 5 and 9 days after treatment with the cheese whey extract.

In a third investigation on male Golden Syrian hamsters, continuous topical application of GFE-2 to (he hamster cheek pouch reduces the severity of 5-fluorouracil (5-FU)-induced chemotherapy-induced mucositis.

Some aspects of the compositions and methods described herein are described in U.S. patent application Ser. No. 07/956,759, filed Dec. 7, 1992, the complete disclosure of which is incorporated herein by reference.

EXAMPLE 1

Preparation of a Fraction from Cheese Whey (GFE) that is Enriched in Growth Promoting Activity Pasteurized whey obtained as an end product of cheese manufacture was filtered through a 10 micron screen and a 0.2 micron Sartorius Microsart Sartocon II module to remove solids. The ultrafiltrate was adjusted to pH 6.5 and applied to a column of S-Sepharose Fast Flow S cation exchange resin (Pharmacia) that had been equilibrated with 50 mM sodium citrate buffer at pH 6.5. After washing the column with the same buffer the absorbed material was eluted by a solution of 1M NaCl containing 0.25 M $NH_4OH$. This eluate was diafiltered against water until the conductivity reached 0 µg and then concentrated by ultrafiltration; both processes using a 3 kDa-excluding membrane. The resultant preparation was freeze-dried to produce the "GFE" product.

A preparation from 30 liters of cheese whey containing 18 g protein yielded a GFE extract containing 2.66 g protein.

EXAMPLE 2

Preparation of a Fraction from Cheese Whey that is Enriched in Growth-promoting Activity and Depleted in Extraneous Protein Including Lactoferrin (GFE-2)

Pasteurized whey was filtered and applied to a column of S-Sepharose and the column washed as in Example 1. Elution was accomplished with a solution containing 0.4M NaCl added to 10 mM sodium citrate pH6.5. This GFE-2 was diafiltered against water, concentrated and freeze-dried as described in Example 1.

A preparation from 30 liters of cheese whey which contained 18 g protein yielded a GFE-2 extract containing 0.56 g protein.

EXAMPLE 3

Preparation of a Modified GFE-2 Fraction that is also Depleted in Extraneous Protein Including Lactoperoxidase (GFE-3)

The freeze-dried GFE-2 (Example 2) was dissolved at a concentration of 25 mg/ml and heated at 80° C. for 2.5 min. The heated sample was cooled rapidly and centrifuged. The clear supernatant was passed through a 0.22 µm filter before use. This solution contained 50% of the protein present in GFE-2 and approximately 10% lactoperoxidase.

EXAMPLE 4

Stimulation of the Growth of Cultured Cells by Cheese Extracts (Examples 1.2) Compared with Fetal Bovine Serum Prior to the addition to culture media, the freeze-dried powders (GFE, GFE-2) were first suspended in Dulbecco's Phosphate-buffered saline and sterilized by passage through a 0.2 µm filter.

This example utilizes the cell lines L6 (rat myoblast), Balb C/3T3 (mouse fibroblast) and SF1972 (human diploid skin fibroblast).

Each cell line was subcultured on to 96-place tissue culture plates in Dulbecco-Modified Eagle's Minimal Essential Medium (DMEM) containing 5% fetal bovine serum and left in a 5% $CO_2$, 37° C., humidified incubator overnight to ensure attachment of the cells. Sterile techniques were used throughout. The plates were thoroughly washed in DMEM to remove any residual serum and the whey extract (GFE or GFE-2) or fetal bovine serum (FBS) added at the indicated concentrations. The total volume in each well was 0.1 ml at 37° C., 5% $CO_2$ and 100% humidity.

Figure 1A:
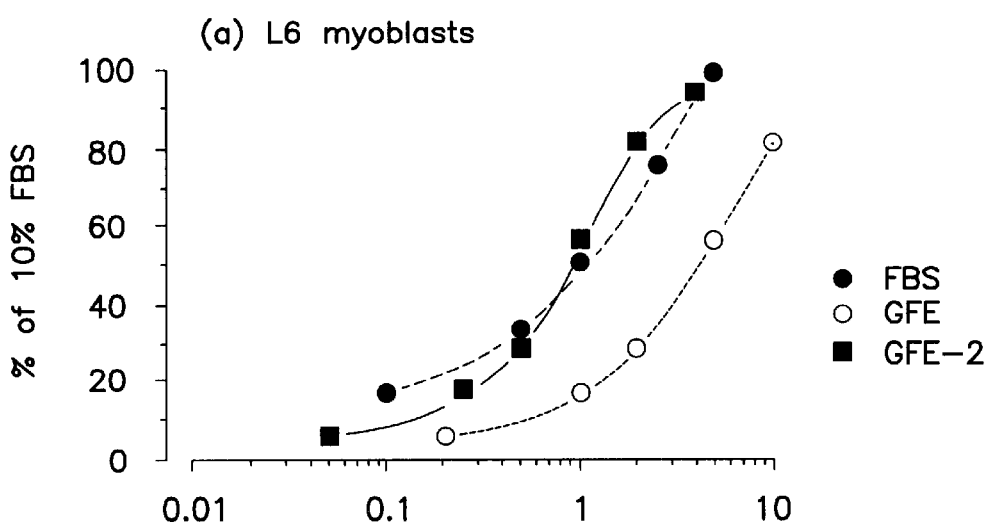
FIG. 1
Figure 1B:
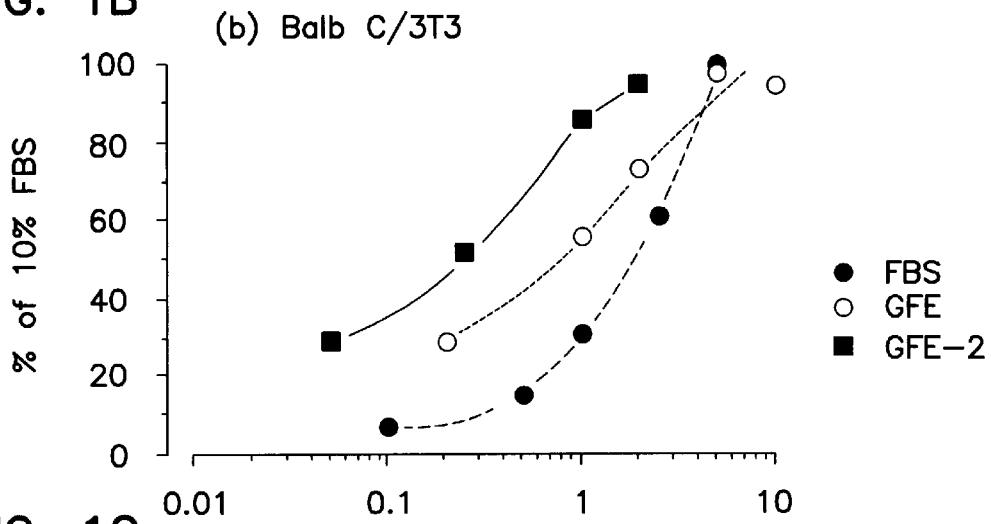
Figure 1C:
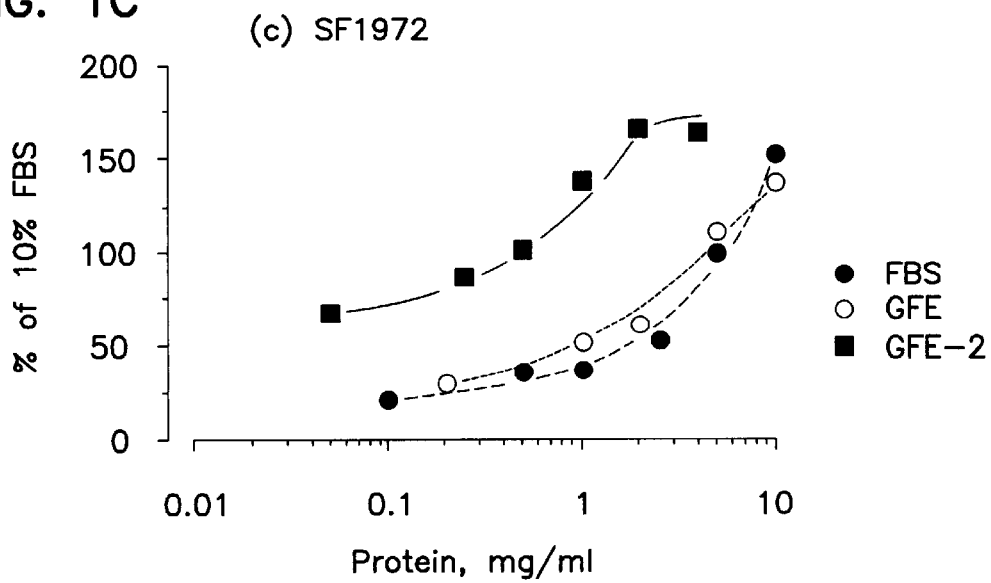

After a further 2 days the plates were washed, fixed and the cell numbers quantified using an automated methylene blue method (M. H. Oliver et al., J. Cell Sci. 92, 513, 1989). Growth is expressed as the percentage increase in absorbance units relative to the increase in absorbance produced by growing the cells in DMEM containing 5% fetal bovine serum (FIG. 1).

This example shows that in all three cell lines GFE and GFE-2 stimulate growth as well as fetal bovine serum. Moreover, in Balb C/3T3 and SF1972 cells GFE-2 is active at approximately one tenth the protein content as fetal bovine serum.

EXAMPLE 5

Stimulation of the Growth of Cultured Cells by Extracts of Cheese Whey Depleted in Extraneous Protein Including Lactoperoxidase (GFE-3, Example 3) Compared with GFE-2 (Example 2)

The experimental details were exactly as described in Example 4 except that the data are expressed as the protein content ($\mu$g/100 $\mu$l well) that achieved the same growth response as was achieved with 5% fetal bovine serum (see Table 1).

TABLE 1

Growth of Cells in the presence of GFE-2 or GFE-3

| Cell Type | Extract | Concentration ($\mu$g/100 $\mu$l) achieving growth equivalent to 5% fetal bovine serum |
| --- | --- | --- |
| L6 | GFE-2 | 100 |
|  | GFE-3 | 63 |
| Balb C/3T3 | GFE-2 | 15 |
|  | GFE-3 | 6 |
| SF1972 | GFE-2 | 8 |
|  | GFE-3 | 4 |

Clearly less GFE-3 is required to stimulate growth than GFE-2. Also since 5% fetal bovine serum has a protein content of 250 $\mu$g/100 $\mu$l, both GFE-2 and GFE-3 are very substantially more potent than 5% fetal bovine serum, especially for Balb C/3T3 cells and human skin fibroblasts (SF1972).

EXAMPLE 6

Growth Effects of Cultured Cells Produced by Supplementing Medium Containing 2% Fetal Bovine Serum with GFE-2 extracts (Example 2)

The experimental details were exactly as described in Example 4 except that the human lung fibroblast line (HEL) replaced the human skin fibroblast line (SF1972). Data are expressed as absorbances achieved after growth of the cells for 2 days (see Table 2).

TABLE 2

Growth of Cells with GFE-2 added in the presence of 2% fetal bovine serum

| Fetal Bovine Serum (%) | GFE-2 ($\mu$g/100 $\mu$l) | Increases in absorbance | | |
| --- | --- | --- | --- | --- |
| | | L6 cells | Balb C/3T3 cells | HEL cells |
| 2 | 0 | 0.618 | 0.126 | 0.16 |
| 5 | 0 | 0.998 | 0.270 | 0.21 |
| 10 | 0 | 1.309 | 0.502 | 0.34 |
| 2 | 5 | 1.010 | 0.294 | 0.32 |
| 2 | 25 | 1.108 | 0.585 | 0.38 |
| 2 | 50 | 1.157 | 0.698 | 0.38 |
| 2 | 100 | 1.370 | 0.799 | 0.37 |

This experiment demonstrates that low amounts of GFE-2 added to medium containing only 2% fetal bovine serum can increase the growth rate to that achieved with 10% fetal bovine serum. The approximate amount of GFE-2 required to achieve this growth enhancement was 100 $\mu$g/100 $\mu$g in L6 cells, 25 $\mu$g/100 $\mu$l in Balb C/3T3 cells and only 5 $\mu$g/100 $\mu$l in HEL cells. Such an enhancement represents a very substantial saving of fetal bovine serum.

EXAMPLE 7

Cheese Whey Extract Contains Factors that Promote DNA Synthesis by Cultured Human Endothelial Cells GFE-2 was prepared as in Example 2. The GFE-2 was dissolved in M199 medium, passed through a 0.22 micron filter, and serially diluted in the same medium.

Figure 2:
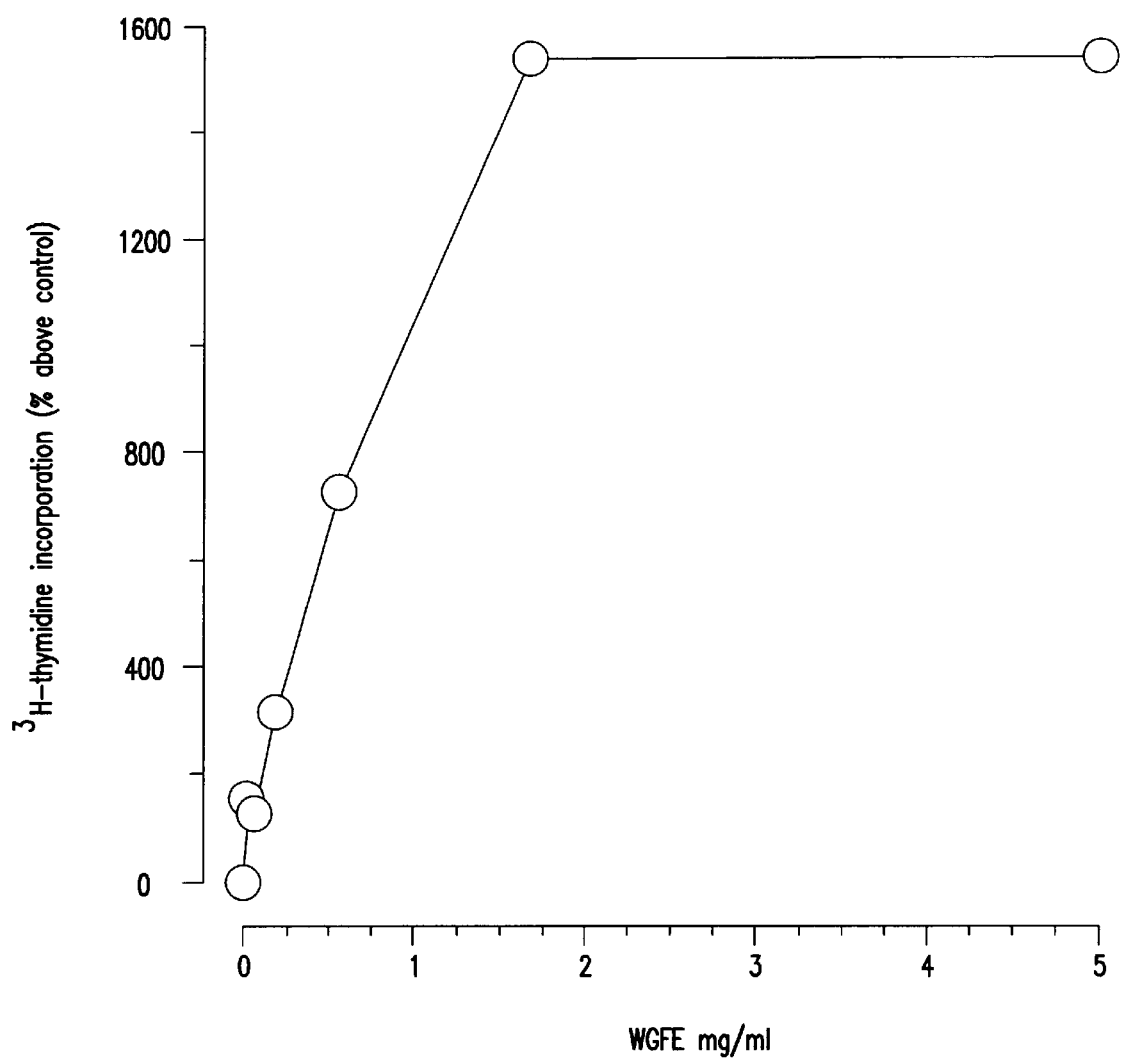

This example utilizes human umbilical vein endothelial cells as a primary cell of wound repair. Primary cultures of human umbilical vein endothelial cells were isolated according to the method of Gimbrone et al. (J. Cell. Biol. 60, 673, 1974) and passaged in medium 199 containing 20% FBS, endothelial cell growth supplement, and heparin, and left in a 5% $CO_2$, 37° C. humidified incubator overnight to ensure attachment of the cells. Sterile techniques were used throughout. The plates were then thoroughly washed in M199 to remove any residual serum and the whey extract added at the indicated concentrations. The total volume in each well was 1 ml. After a 24 h incubation $^3$H-thymidine was added to each well and allowed to incorporate into cellular DNA for a further 6 h. The cells were then washed thoroughly to remove unincorporated $^3$H-thymidine and the cell layer dissolved in 0.5M NaOH containing 0.1% Triton x_100. $^3$H-Thymidine incorporated into cellular DNA was measured by scintillation counting. DNA synthesis is expressed as the percentage increase in cpm above that produced by growing the cells in unsupplemented M199 (FIG. 2).

This example shows that the cheese whey extract contains factors that stimulate DNA synthesis by endothelial cells. The growth response exerted by cheese whey extract can be distinguished from transforming growth factor beta which inhibits the growth of endothelial cells (Muller et al. "Inhibitory action of transforming growth factor beta on endothelial cells". Proc. Natl. Acad. Sci. USA 84, 5600, 1987).

EXAMPLE 8

Cheese Extract Induces Contraction of a Fibroblast-populated Collagen Lattice

GFE-2 was prepared as in Example 2, and sterile filtered by passage through a 0.22 $\mu$m filter.

Figure 3:
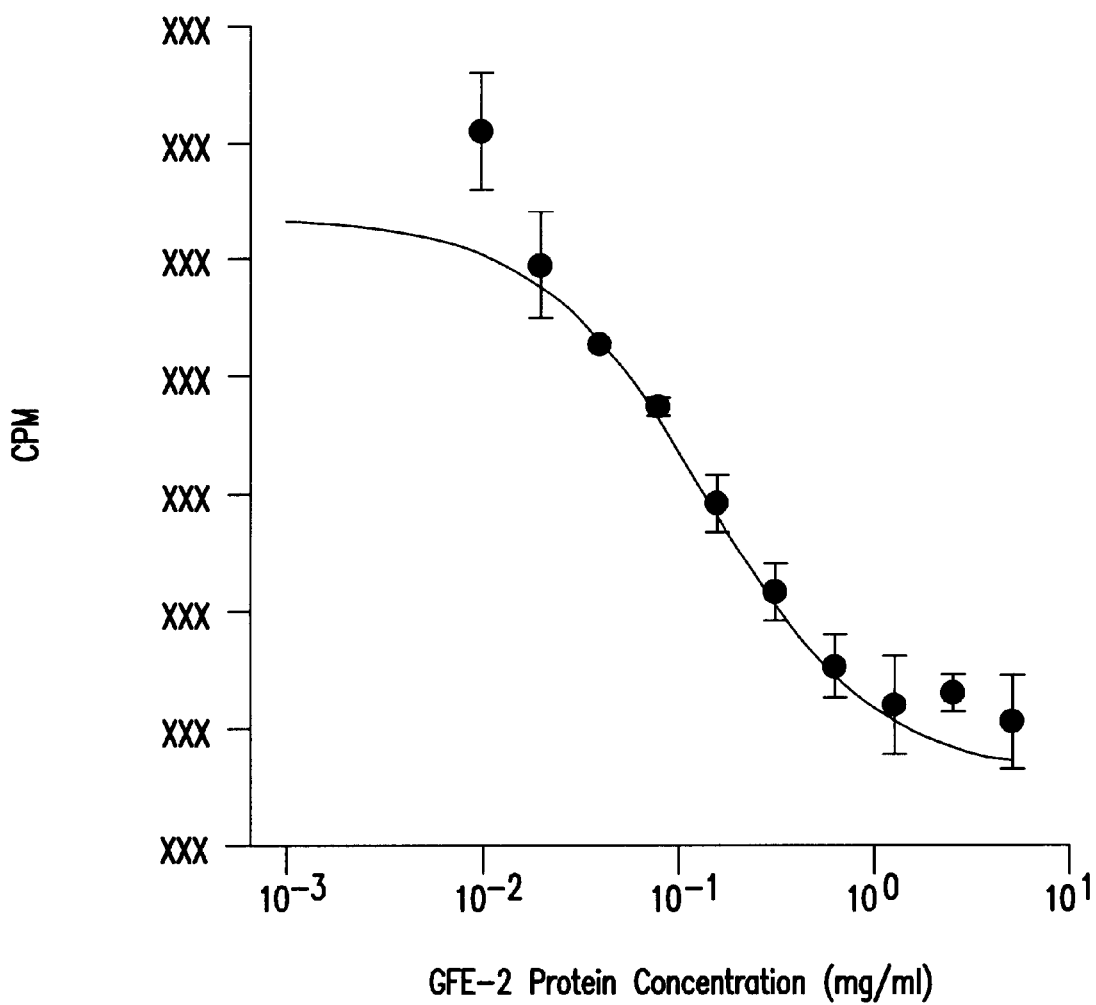

An in vitro model of wound contraction was prepared as follows. Human diploid skin fibroblasts were suspended in Dulbecco's-Modified Eagle's Minimal Essential Medium (DMEM) at a concentration of 200,000 cells per ml, and mixed with an equal volume of soluble rat tail collagen (2 mg per ml) containing $^3$H-inulin (10–20,000 cpm per ml). The mixture was poured into 24-place wells (1 ml per well) and allowed to gel by incubation at 37° C. for 30 minutes. The gels were then separated from the tissue culture plastic by reaming the margin of the gel with a 25G needle. The fibroblast populated collagen matrix was then overlaid by DMEM containing cheese whey extract at the indicated concentrations and incubated for a further 24 hours at 37° C. in a humidified atmosphere containing 5% $CO_2$. The degree of collagen contraction was determined by scintillation counting of the $^3$H-inulin remaining in the contracted gel (means+SEM, N=3, FIG. 3).

This example shows that factors in cheese whey extract act on the human skin fibroblast to induce reorganization of collagen fibers and contraction of a collagen gel that is analogous to the contraction of a wound.

EXAMPLE 9

Whey-derived Growth Factor Extract Induces Closure of a Full Thickness Excisional Wound in Cultured Fetal Rat Skin Cheese whey extract GFE-2 as produced in Example 2 was dissolved in Dulbecco's-Modified Eagle's Minimal Essential Medium (DMEM) and sterile filtered.

Figure 4:
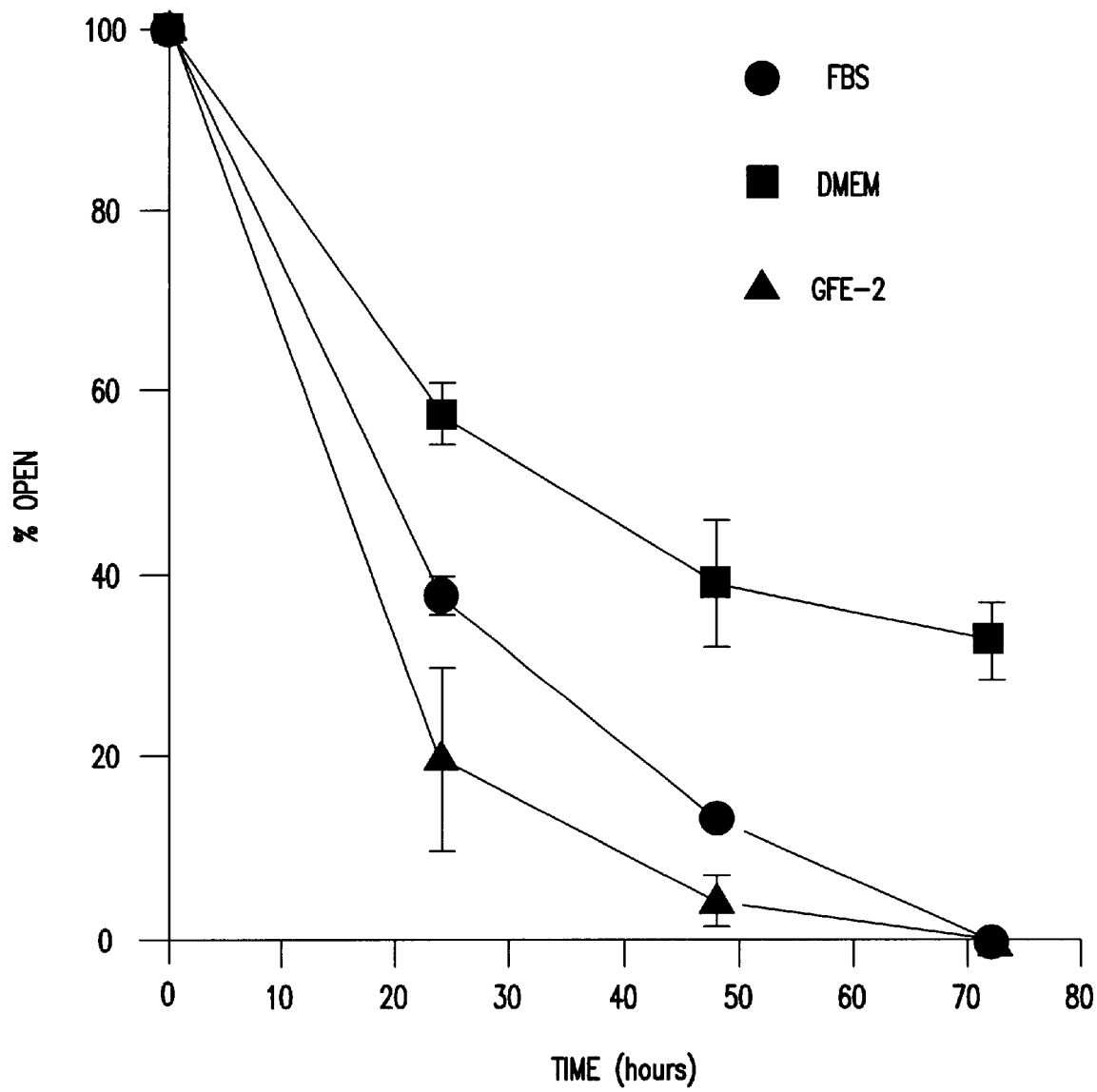

An in vitro organ culture model of wound repair was established as follows. A pregnant Sprague-Dawley rat was killed by $CO_2$ asphyxiation at 17 days gestation and fetal rats dissected free from the uterus. A 1 cm×1 cm piece of skin, including the epidermis and fill thickness dermis, was dissected from the back of each fetus using fine scissors and forceps, and a 1 mm hole placed in the centre of the skin using a 19G needle. The preparation was mounted on a cradle and placed in a culture dish containing DMEM done, dilutions of cheese whey extract or 10% fetal bovine serum (FBS). All preparations were photographed using a standard focal length jig prior to culture. Cultures were then maintained at 37° C. in a humidified atmosphere of 5% $CO_2$ for 72 hours, and photographed at 24, 48 and 72 hours. The percentage of the wound remaining open was determined by planimetry. FIG. 4 shows that cheese whey extract at a concentration of 2.5 mg/ml is able to induce healing of the excisional defect after 72 h culture (mean+SEM, N=3). This experiment shows that cheese-whey extract contains factors that promote healing of a full thickness excisional wound in organotypic fetal skin culture.

EXAMPLE 10

Cheese Whey Extract Enhances Wound Strength in Normal Rats

Cheese whey extract GFE-2 prepared as in Example 2 was formulated in a 1 mg/ml collagen solution to a final concentration of 2.5 mg/ml.

Figure 5:
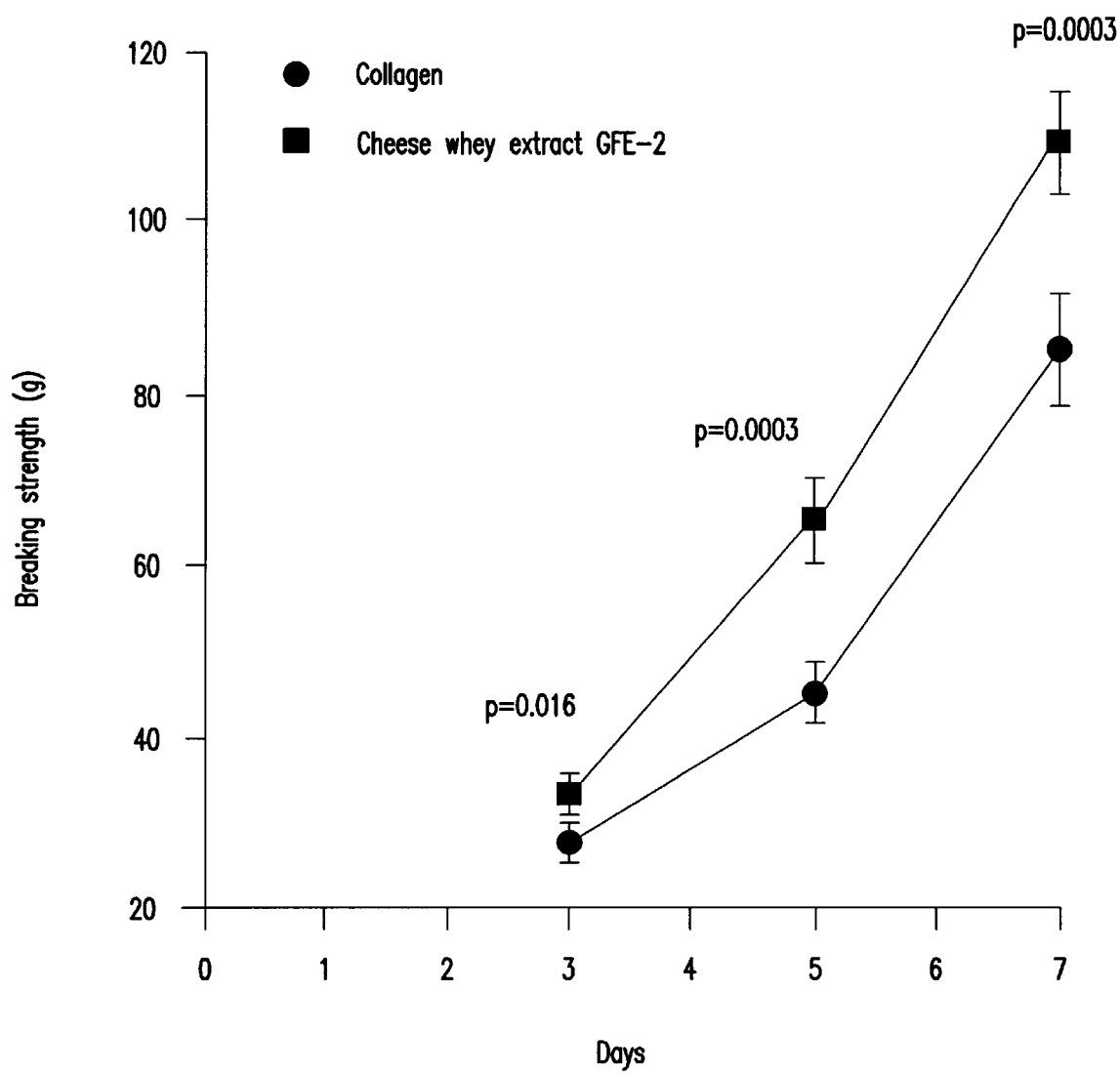

An in vivo model of incisional wound repair was established as follows. Male rats between 250 and 300 g were anaesthetized by inhalation of isofluorane and paired 6 cm full thickness incisions were placed through the skin 1.5 cm either side of the dorsal midline. Cheese whey extract (2.5 mg/ml) was then applied to one wound and vehicle (rat tail collagen, 1 mg/ml) applied to the contralateral wound, each rat therefore serving as its own control. Each wound received 100 μl of either the vehicle or the cheese whey extract preparation; experimental wounds therefore received 250 μg of cheese whey extract. The margins of both wounds were then apposed using sutures and animals housed individually after surgery. Rats were killed by $CO_2$ asphyxiation at days 3, 5 and 7, and the dorsal pelts removed. The maximum load (breaking strength) tolerated by the wounds was measured by placing 4 mm strips taken at 90° to the wound in a tensiometer. Wound strength (mean+SEM, N=16 wounds per time point) is expressed as breaking strength vs time (FIG. 5).

This example shows that the single application of cheese whey extract enhances healing of an incisional wound in normal rats. This enhancement is particularly evident between 3 and 5 days after wounding, and is maintained until day 7.

EXAMPLE 11

Cheese Whey Extract Enhances Wound Contraction and Epithelialization in Steroid-treated Rats Cheese whey extract was prepared as in Example 2 and formulated as in Example 10.

An in vivo model of wound contraction and epithelialization was established as follows. Sprague Dawley rats, weighing between 250 and 300 grams were administered methyl-prednisolone (30 mg/kg). The rats were then anaesthetized using isofluorane/$N_2O/O_2$, their backs clipped of hair and four square symmetrical wounds created down the midline of the back. A template containing four square holes, each measuring 1.5 by 1.5 cm, was used to create a line of wounds through the skin and panniculus camosis muscle to the deep fascia of the back. The size and shape of the wounds are then recorded by taking analogue tracings onto acetate film. All rats were housed individually after surgery. Animals were reanaesthetized and wound areas measured on days 1, 3, 5, 7, 9, 12, 14, 16, 19, 21, 23, 26 and 28. Care was taken to delineate between the full thickness wound margin and the advancing epithelium which were recorded separately. Wounds were treated with the vehicle preparation (rat tail collagen at 1 mg/ml) or vehicle plus whey extract, daily for the first 10 days of the study. A further control group received no treatment and the wounds were left exposed. Data (means±SEM, N=28 wounds) are expressed as area inside full thickness wound margin vs time (FIG. 6(a); wound contraction) or area inside the epithelial margin of the wound vs time (ie incorporating wound epithelialization; FIG. 6(b)).

This experiment shows that cheese extract incorporated into a collagen vehicle enhances wound contraction and epithelialization in steroid-compromised animals.

EXAMPLE 12

Cheese Whey Extract Contains Factors that Promote Cell Division by Cultured Intestinal Epithelial Cells GFE-2 was prepared as in Example 2. The GFE-2 was dissolved in Dulbecco's Modified Eagle's Medium (DMEM), passed through a 0.22 micron filter, and serially diluted in the same medium.

This example utilizes rat intestinal epithelial cells as a primary cell of intestinal wound repair. IEC-6 cells were maintained and passaged in DMEM containing 10% FBS. For each experiment, IEC-6 cells were sub-cultured onto 96-place tissue culture plates in DMEM containing 10% FBS and left in a 5% $CO_2$, 37° C. humidified incubator overnight to ensure attachment. Sterile techniques were used throughout. The plates were then thoroughly washed in DMEM to remove any residual serum and the whey extract added at the indicated concentrations either alone or in the presence of 1% FBS or 5% FBS. The total volume in each well was 0.1 ml. After a 48 h incubation period the cell number was assessed using a dye-binding assay (Oliver et al., J. Cell. Sci. 92, 513, 1989).

This example shows that the whey extract contains factors that stimulate growth of intestinal epithelial cells, and therefore whey extract may be useful in promoting repair of intestinal ulceration or damage, or to enhance intestinal growth.

EXAMPLE 13

Oral Administration of a Milk Product Extract from Bovine Cheese Whey (CGE-2) Partially Prevents Loss of Small Intestinal Crypts and Villi in Rats with Methotrexate Induced Small Bowel Damage In this Example 13, rats were injected with high doses of the chemotherapy agent, methotrexate, as an experimental model of damage to the lining of the alimentary tract. Oral administration to methotrexate-injected rats of a milk product extract purified from bovine cheese whey (GFE-2 as described in Example 2) provides evidence that the milk product extract can ameliorate chemotherapy damage to the small bowel.

Male Sprague Dawley rats, weighing on average 140 g and maintained in metabolism cages were fed a high-carbohydrate diet. Control rats received no GFE-2 whereas experimental rats were treated for 5 days with GFE-2. GFE-2 treated rats were fed a modified diet containing 31.2 g GFE-2/kg diet in place of the equivalent amount of casein. In addition, the GFE-2 fed rats were given GFE by stomach gavage on days 3, 4 and 5 of the experimental period so that the total dose of GFE-2 per day averaged 514 mg/day GFE-2. Control rats were fed the unmodified diet and gavaged by an identical protocol on days 3, 4 and 5 with an equivalent amount of bovine serum albumin to ensure an isonitrogenous diet.

One group of control rats and the GFE-2 treated rats (8 rats per group) were injected subcutaneously with 2.5 mg/kg methotrexate at the start of days 1, 2 and 3. An additional control group ("pair-fed") received sham methotrexate injections, and was pair-fed to the methotrexate-injected control group.

Rats were maintained in the metabolism cages for 5 days, at which time they were killed for collection of the gastrointestinal tract. Tissue samples were collected from the proximal small bowel (duodenum and jejunum) as well as the distal small bowel (ileum). Tissue samples were fixed in methacarn, embedded in paraffin, sectioned and stained with haematoxylin-eosin for histological analysis.

Compared with the pair-fed controls, the methotrexate-injected control group showed loss of mucosal crypts in the jejunum, and to a lesser extend in the ileum. This is illustrated in FIG. 8(a) as the area of intact crypts per unit area of total mucosa, and demonstrates that methotrexate causes loss of mucosal crypts (which contain the dividing cells of the epithelium) characteristic of chemotherapy damage. Also characteristic of chemotherapy damage in the small bowel, methotrexate injection caused stunting and loss of intestinal villi, being the functional compartment of the small bowel mucosa. This is illustrated in FIG. 8(b) by a reduction in the surface length of the finger-like villi per unit length of intestinal circumference in methotrexate-treated controls compared with the pair-fed group receiving no methotrexate.

Figure 8:
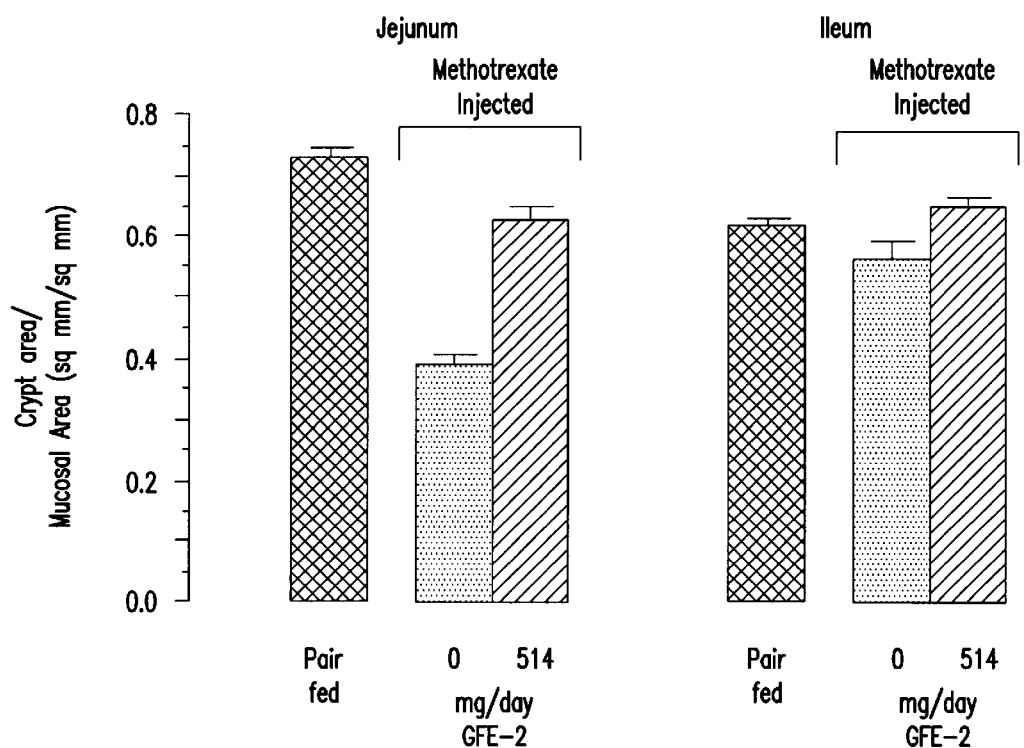
Figure 8:
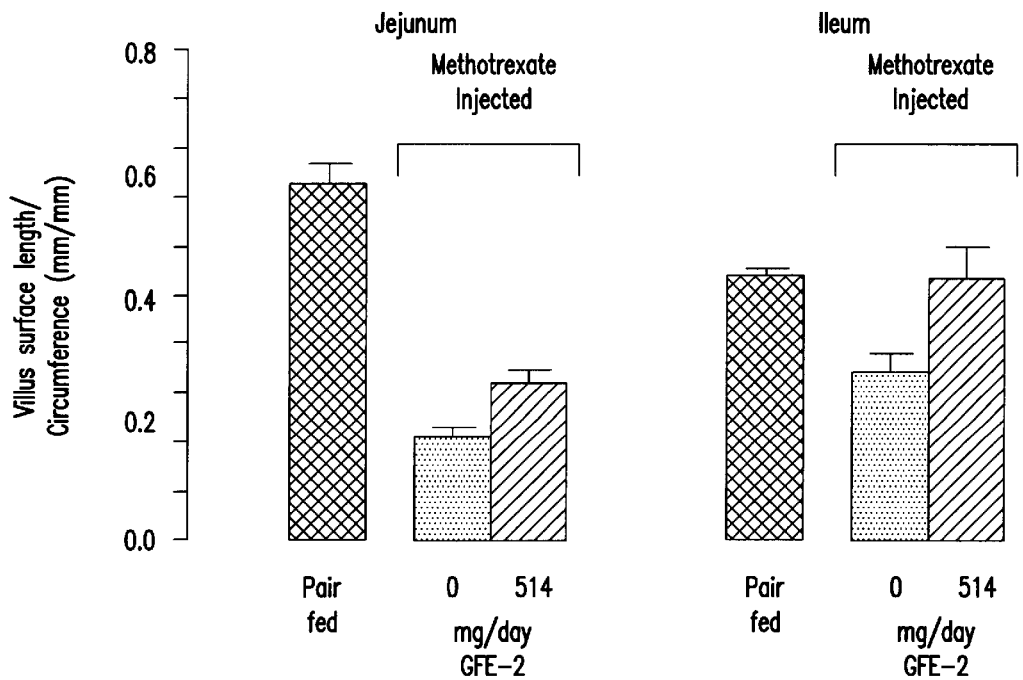

Oral administration of GFE-2 for 5 days starting at the time of the first methotrexate injection partially prevented the loss of mucosal crypts and villi in both regions of the small bowel (FIG. 8). The effects of GFE-2 were statistically significant ($P<0.05$ by ANOVA) in the jejunum, where methotrexate-induced damage was more severe, and in the ileum for villus surface length.

The example demonstrates that oral administration of GFE-2 is able to partially prevent or accelerate repair of chemotherapy damage in the small bowel.

EXAMPLE 14

Sucrase Activity is Increased in the Damaged Mucosa of Rats Treated with Cheese Whey Extract From the same experiment as described in Example 13, 4 cm lengths of small bowel were frozen for measurement of the activity of mucosal sucrase, an enzyme located on the surface of epithelial cells of the villus. Because sucrase is essential for digestion of dietary sucrose, the sucrase activity per unit length of intestine provides a measure of the functional capacity of the small bowel.

Figure 9:
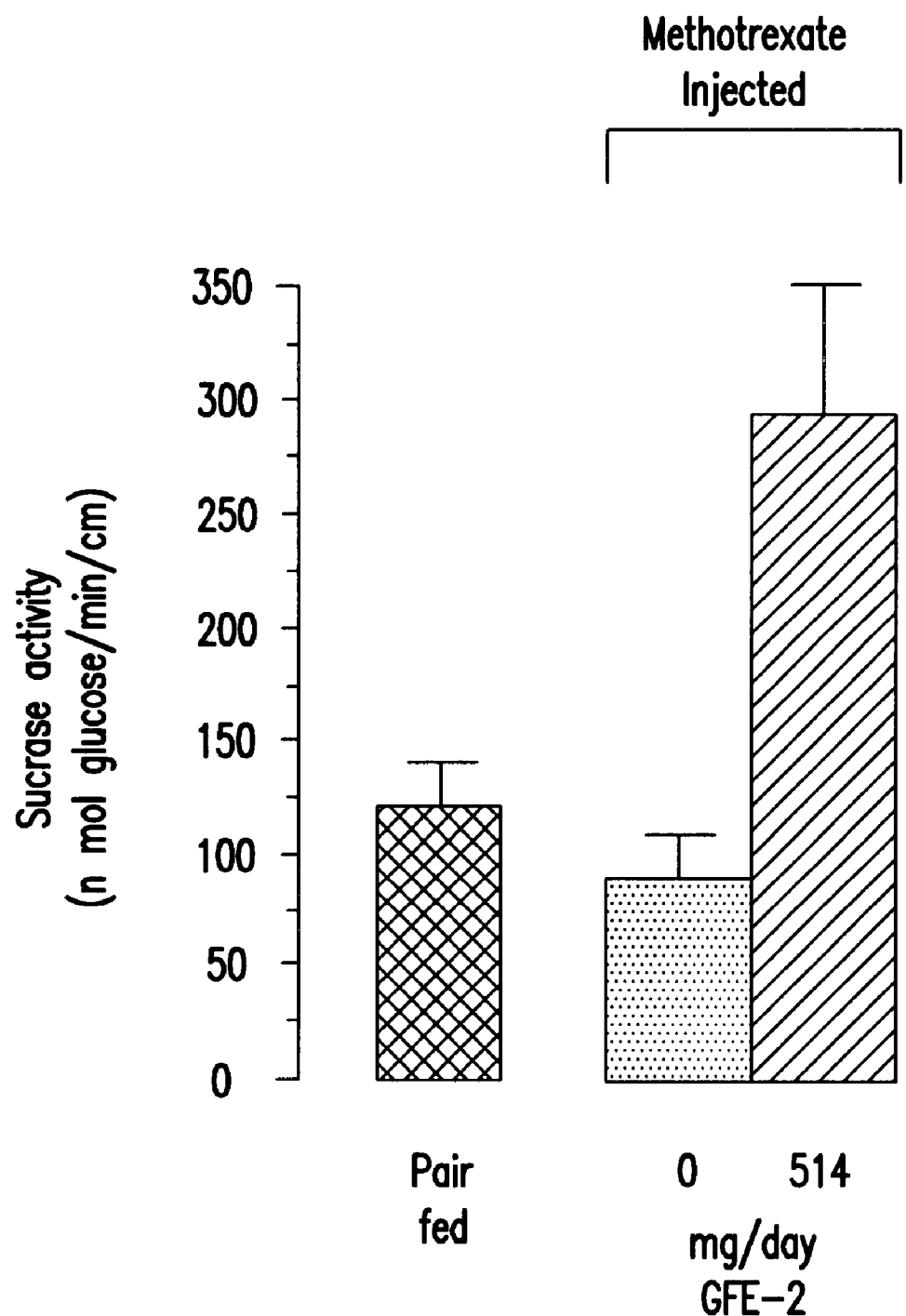

Five days' oral administration of GFE-2 to methotrexate-injected rats significantly improved ($P<0.05$) the sucrase activity per unit length of ileum compared with the methotrexate-injected control group, or the pair-fed control group (FIG. 9).

This example demonstrates that GFE-2 improves the functional capacity of the chemotherapy-damaged small bowel.

EXAMPLE 15

Oral Administration of Cheese Whey Extract to Rats for 5 to 12 Days Reduces Bacterial Translocation Across the Gut The ability of the gut epithelium to provide a barrier against bacterial invasion provides another measure of gut function that is improved by cheese whey extract.

140 g male Sprague Dawley rats were injected with methotrexate for three consecutive days as described in Example 13. Methotrexate-injected rats were administered oral GFE-2 by an identical protocol to that described in Example 13. One group of rats was killed on day 5 after the start of methotrexate injections (as in Example 13), while in other groups, GFE-2 treatment was continued for a total of 8 or 12 days (8 rats per group). Control methotrexate treated rats and pair-fed control rats identical to those in Example 13 were killed on days 5, 8 and 12 (8 rats per group).

Rats were maintained in metabolism cages as in Example 13 until exsanguination on day 5, 8 or 12. The abdominal skin was soaked in 70% ethanol before the intestine was removed under aseptic conditions. All visible mesenteric lymph nodes were placed into a sterile pre-weighed container. Samples were then weighed and infusion solution was added to a final concentration of 100 mg/ml. Tissues were homogenized in this solution with sterile glass-reinforced grinders. For measurement of translocation of gram negative bacteria into mesenteric lymph nodes, 40 or 60 mg of each tissue homogenate was placed onto MacConkey agar II or blood agar plates and incubated aerobically at 35° C. for 48 hours. Enteric gram negative bacterial colonies were identified using API 20E strips, then counted. The incidence (proportion of animals exhibiting detectable bacterial translocation) and mean number of bacterial colonies per gram of tissue were calculated for each treatment group.

Figure 10:
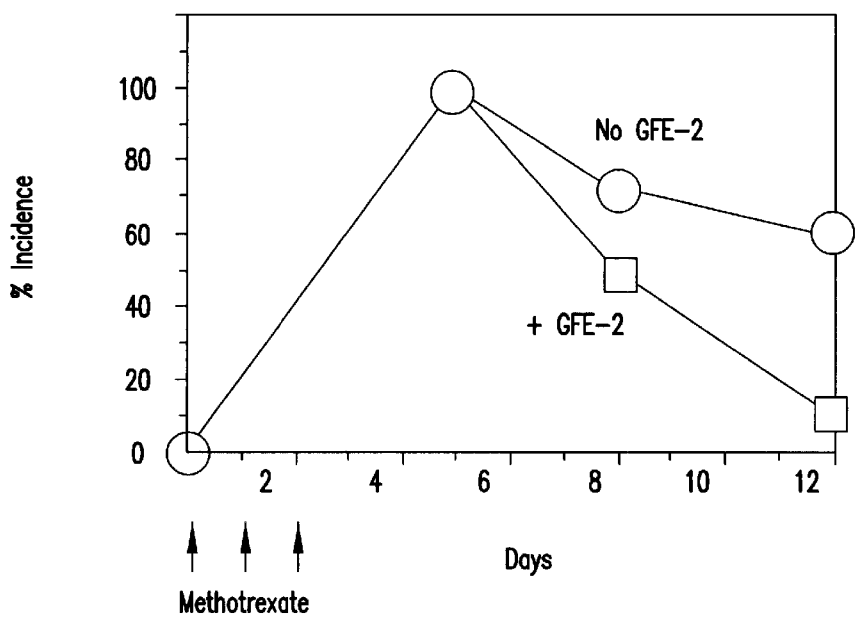
Figure 10:
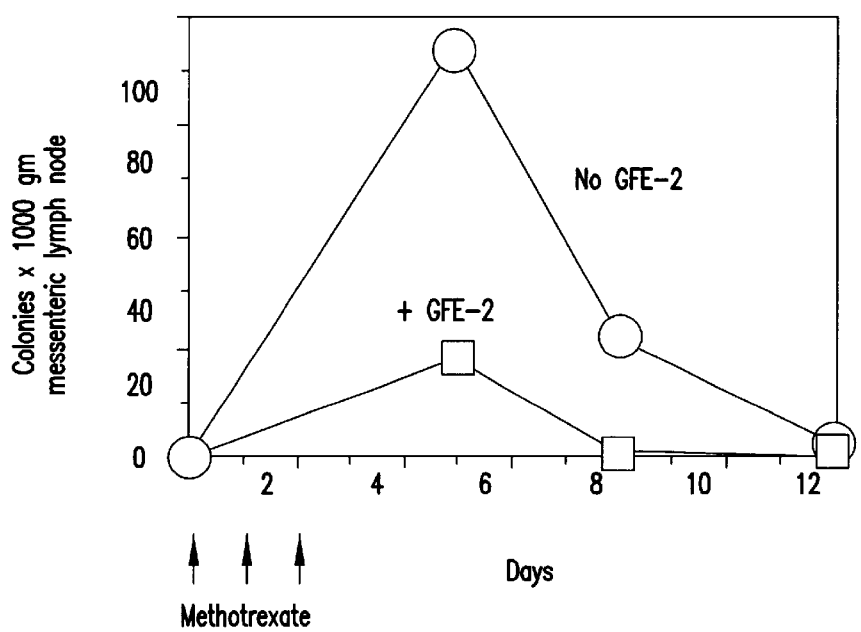

Pair fed control animals receiving no methotrexate showed no incidence of bacterial translocation across the gut. Methotrexate injection impaired the intestinal barrier so that all rats in the methotrexate-injected control group (FIG. 10; "No GFE-2") had positive bacterial cultures from mesenteric lymph nodes on day 5. The incidence in this group diminished over the next 7 days, but remained at 60% on day 12 (FIG. 10(a)). The number of colonies per gram of mesenteric lymph node was maximal on day 5, and then diminished thereafter in parallel with the incidence (FIG. 10(b)).

Oral administration of GFE-2 resulted in a lower incidence of translocation on days 8 and 12, with the difference between GFE-2 treated and control 2 methotrexate-injected rats reaching statistical significance by $X^2$ test (P<0.05) on day 12. The number of colonies per gram of mesenteric lymph node was also significantly lower in the GFE-2 treated group on both day 5 and 8.

The example demonstrates that oral administration of the milk product extract partially prevents chemotherapy-induced loss of barrier function in the gut. This could be expected to decrease the incidence of infection and sepsis following chemotherapy.

Finally, it is to be understood that various other modifications and/or alterations may be made without departing from the spirit of the present invention as outlined herein.

EXAMPLE 16

Continuous Topical Application of GFE-2 to the Hamster Cheek Pouch Reduces the Severity of 5-fluorouracil (5-FU)-induced Chemotherapy-induced Mucositis This experiment investigated the effects of GFE-2 administered topically on chemotherapy-induced oral mucositis in male Golden Syrian hamsters. The trial included continuous treatment of GFE-2 to the cheek pouch of 10 hamsters treated with 5-fluorouracil.

Hamsters were divided into two groups of five animals. The initial mean body weight of each group was similar. All hamsters were given intraperitoneal injections of 90 mg/kg of-5-FU on day 1, and 60 mg/kg on day 3. The cheek pouch was scratched on days 1, 2 and 3 with six strokes of a wire brush in one direction and six strokes in the other perpendicular direction to achieve a uniform wound.

Groups were treated with either a commercial mouthwash as vehicle, or 0.3 ml of GFE-2 at 40/mg/ml protein concentration. The cheek pouch liquid treatments were applied daily for one minute, during which time the hamsters were anaesthetized using isoflurane anesthesia.

The cheek pouch was assess on days 5, 7, 8, 11, 13 and 15. Monitoring was 30 based on a visual assessment of the cheek pouch (graded on a 1–10 scale) taking into account the overall severity of the lesion, degree of bruising, swelling and scarring. Body weight was recorded as a percentage of the day 0 value.

Figure 11:
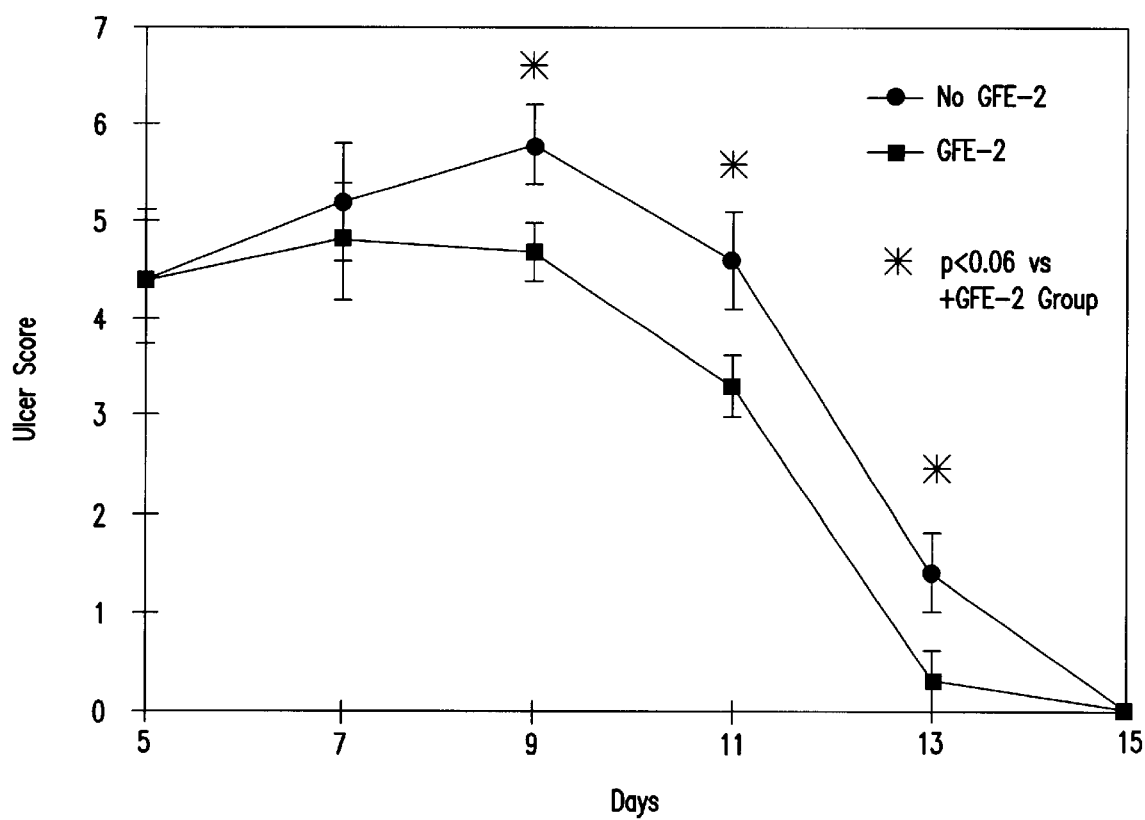
Figure 12:
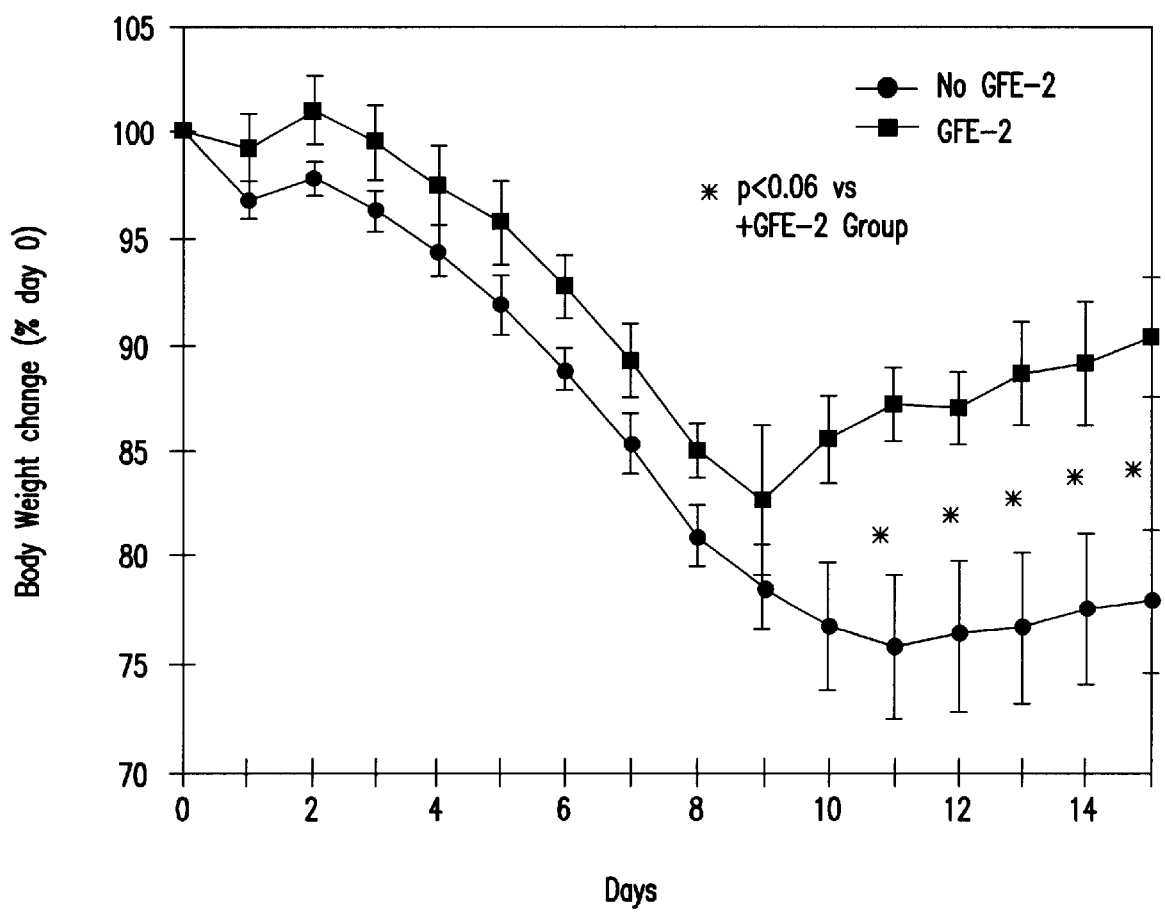

Animals given a topical treatment of GFE-2 showed reduced mucositis compared to the vehicle treated group, measured as overall visual score (FIG. 11), total ulcer area and body weight loss (FIG. 12). Each of these effects was statistically significant by paired t-test favoring GFE-2 treatment.

This example suggested that topical administration of GFE-2 may reduce the severity of oral mucositis and related symptoms such as body weight loss.

EXAMPLE 17

Large Scale Preparation of a Fraction from Cheese Whey that is Enriched in Growth-promoting Activity and Depleted in Extraneous Protein Including Lactoferrin (GFE-2)

Pasteurized whey obtained as an end product of cheese manufacture was clarified by passage through a 0.8 $\mu$m ceramic filter (Membralox, Bajet, France). The ultrafiltrate was adjusted to pH6.5 and 2300 liter applied through a stream-splitting value to 2 columns in parallel, each column having a diameter of 30 cm and filled with 12.5 liters of S-Sepharose Big Beads cation exchange resin (AMRAD Pharmacia Biotech) equilibrated with 10 mM sodium citrate buffer at pH 6.5. After washing the columns with 4 column volumes of water, the adsorbed growth factors were eluted with 115 liters of 0.4 M NaCl containing 10 mM sodium citrate pH6.5. This eluate was diafiltered and concentrated against 0.15M NaCl to a protein concentration of approximately 40 g/liter, filter sterilized by passage through a 0.2 $\mu$m filter and stored at −20° C.

The yield of protein containing growth promoting factors was 130 grams.

EXAMPLE 18

Test Evaluation of a Cation-exchange Resin for its Suitability for Selectively Adsorbing Growth Promoting Factors from Cheese Whey Pasteurized cheese whey was processed and the growth promoting factors eluted according to Example 1. Subsequently the whey that had passed through the column ("flow-through fraction") was reapplied to the cation-exchange column and a second "flow through" and a second eluate obtained under the same conditions as the first eluate. The five samples (#1, microfiltered whey; #2, 1st "eluate"; #3, 2nd eluate; #4, 1st "flow through"; and #5, 2nd "flow through") were subjected to electrophoresis in the presence of sodium dodecyl sulfate on a 8% to 25% preformed slab gel and stained with Coomassie blue using a Pharmacia Phast System according to the manufacturer's instructions. Molecular mass standards from 29 kDa to 116 kDa were run in a separate lane.

Figure 13:
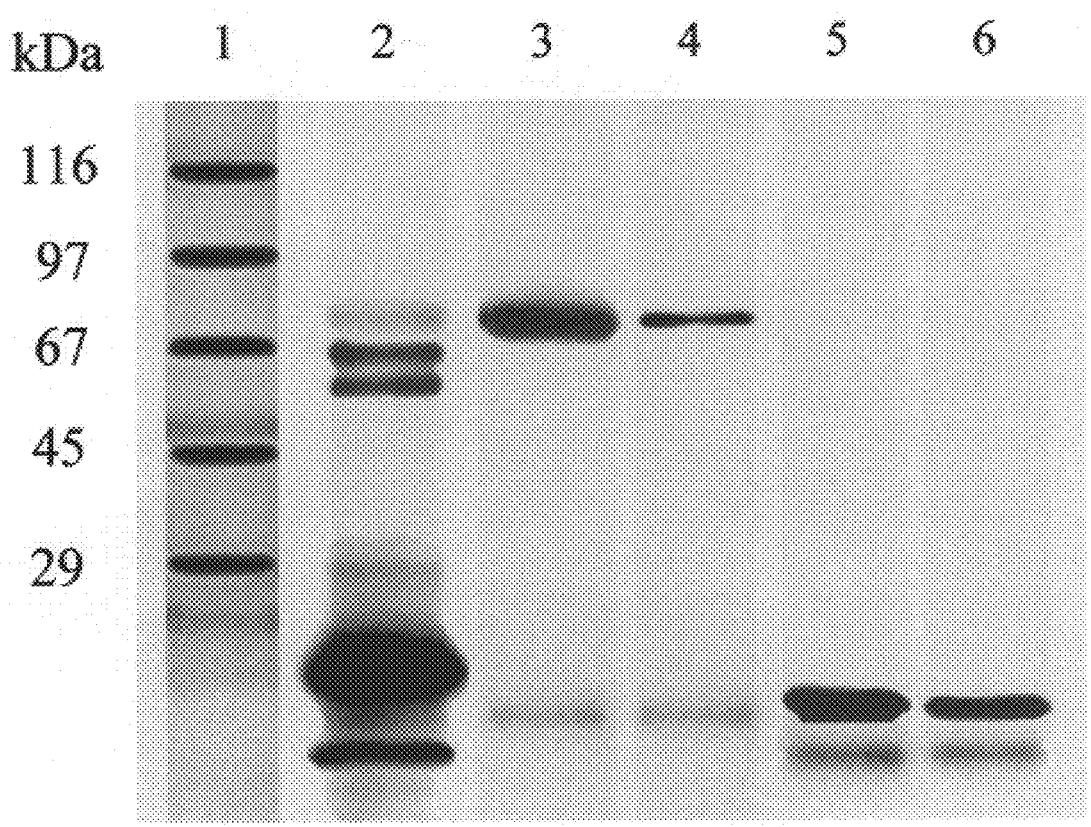

The results are shown in FIG. 13. This figure demonstrates that the bulk of proteins in the cheese whey (lane 2) and in the first and second "flow-through" fractions had molecular masses less than 29 kDa and actual sizes equivalent to those expected for the acidic proteins, alphalactalbumin and beta lactoglobulin. On the other hand the first eluate contained one major protein band of approximately 80 kDa as expected for the basic proteins lactoperoxidase and lactoferrin (lane 3). The second eluate (lane 4) contained the same band but at a much lower concentration since most of the basic protein had been adsorbed on to the column during the first passage of the cheese whey.

This experiment demonstrates the suitability of the Sepharose Fast Flow S cation-exchange resin to selectively bind basic proteins in cheese whey while allowing the abundant acidic proteins to pass through without significant adsorption.

EXAMPLE 19

Preparation of a Fraction from Bovine Skim Milk that is Enriched in Growth-promoting Activity and Depleted in Extraneous Protein Including Lactoferrin (GFE-2)

Bovine skim milk was processed according to the procedure described for cheese whey in Example 2. The yield of skim milk GFE-2 was 74.9 mg protein per liter.

EXAMPLE 20

Preparation of a Fraction from Bovine Colostrum that is Enriched in Growth-promoting Activity and Depleted in Extraneous Protein Including Lactoferrin (GFE-2)

Bovine colostrum was centrifuged to remove fat and undissolved solids and then processed according to the procedure described for cheese whey in Example 2. The yield of colostrum GFE-2 was 339 mg protein per liter.

EXAMPLE 21

Preparation of Milk Growth Factor from Bovine Milk

The procedure described in Example 1(a) of European Patent Application 0313515A1 was used to prepare a preparation of "milk growth factor" or TGF-β2. The "milk growth factor" was processed through the cation-exchange chromatography step using Dowex AG50WX2 50–100 mesh and dried as described in Example 1(a) of European Patent Application 0313515A1. The yield was 4.4 mg of protein per liter.

EXAMPLE 22

Stimulation of the Growth of Cultured Cells by Cheese Whey GFE-2 (Example 2), Skim Milk GFE-2 (Example 19), Colostrum GFE-2 Example 20), Crude Milk Growth Factor (Example 21) and Pure TGF-β (Commercial, from Austral Biologicals, San Ramon, Calif., USA)

The freeze-dried powders of all samples were suspended in Dulbecco's phosphate-buffered saline, sterilized by passage through a 0.22 μm filter and evaluated for cell growth promoting activities according to the method described in Example 4.

The three cell lines utilized were the same as those used in Example 4 except that a different line of human diploid skin fibroblasts (SF 1967) was used. The results are shown below in Table 3.

TABLE 3

Growth of cells with GFE-2 isolated from different milk products and with crude or pure Milk Growth Factor

| Milk Product Extract | Concentration (μg/100 μl) | Cell Growth (increase in absorbance over 2 days; means of 3 ± SEM) | | |
|---|---|---|---|---|
| | | L6 cells | Balb C/3T3 Cells | SF 1967 Cells |
| Cheese Whey GFE-2 | 2 | 0.10 ± 0.02 | 0.19 ± 0.01 | 0.09 ± 0.02 |
| | 8 | 0.16 ± 0.03 | 0.37 ± 0.02 | 0.16 ± 0.02 |

TABLE 3-continued

Growth of cells with GFE-2 isolated from different milk products and with crude or pure Milk Growth Factor

| Milk Product Extract | Concentration (μg/100 μl) | Cell Growth (increase in absorbance over 2 days; means of 3 ± SEM) | | |
|---|---|---|---|---|
| | | L6 cells | Balb C/3T3 Cells | SF 1967 Cells |
| (Example 2) | 34 | 0.20 ± 0.01 | 0.93 ± 0.02 | 0.45 ± 0.03 |
| | 136 | 0.36 ± 0.02 | 1.57 ± 0.02 | 0.74 ± 0.01 |
| Skim Milk GFE-2 | 3 | 0.09 ± 0.00 | 0.29 ± 0.01 | 0.10 ± 0.02 |
| | 11 | 0.18 ± 0.01 | 0.64 ± 0.01 | 0.27 ± 0.02 |
| (Example 19) | 46 | 0.32 ± 0.01 | 1.43 ± 0.02 | 0.85 ± 0.03 |
| | 184 | 0.40 ± 0.01 | 1.43 ± 0.02 | 0.93 ± 0.02 |
| Colostrum GFE-2 | 3 | 0.19 ± 0.01 | 0.37 ± 0.02 | 0.17 ± 0.03 |
| | 11 | 0.24 ± 0.01 | 0.68 ± 0.01 | 0.35 ± 0.04 |
| (Example 20) | 43 | 0.36 ± 0.01 | 1.47 ± 0.03 | 0.67 ± 0.01 |
| | 170 | 0.37 ± 0.01 | 1.89 ± 0.07 | 0.83 ± 0.04 |
| Crude Milk Growth Factor | 0.04 | 0.15 ± 0.00 | 0.05 ± 0.01 | 0.04 ± 0.01 |
| | 0.16 | 0.16 ± 0.01 | 0.10 ± 0.01 | 0.07 ± 0.01 |
| (Example 21) | 0.64 | 0.07 ± 0.03 | 0.27 ± 0.01 | 0.08 ± 0.01 |
| | 2.5 | −0.14 ± 0.00 | 0.27 ± 0.01 | −0.39 ± 0.03 |
| Pure Milk Growth Factor (TGFβ) | 0.01 | 0.01 ± 0.01 | 0.19 ± 0.01 | 0.09 ± 0.02 |
| | 0.04 | 0.03 ± 0.01 | 0.39 ± 0.01 | 0.07 ± 0.02 |
| | 0.16 | 0.06 ± 0.01 | 0.54 ± 0.02 | 0.12 ± 0.02 |
| | 0.63 | 0.04 ± 0.01 | 0.52 ± 0.01 | 0.23 ± 0.02 |

The result of this experiment are the following:

(1) Each of the milk product extracts (GFE-2) obtained from cheese whey, skim milk and colostrum show product substantial and approximately equal amounts of growth stimulation; although each cell type has a characteristic response;

(2) Purified milk growth factor (TGFβ) has no significant growth promoting activity on L6 myoblasts and a weaker response with the other two cell lines than exhibited by GFE-2;

(3) Crude milk growth factor is not effective at stimulating the growth of L6 or SF 1967 cells; indeed growth is inhibited at high concentrations. Growth of Balb C/3T3 cells is stimulated, as for purified TGFβ, but the effect is much smaller than with GFE-2.

The experiment demonstrates the utility of the present invention at obtaining a plurality of growth stimulating factors from different milk products (whey, skim milk, colostrum) and show that the growth effects elicited are markedly different and superior to either crude or pure milk growth factor.

Finally, it is to be understood that various other modifications and/or alterations can be made without departing from the spirit of the present invention as outlined herein. The invention has been described with reference to various specific and preferred embodiments and techniques. However, it should be understood that many variations and modifications may be made while remaining within the spirit and scope of the invention. All publications and patent applications in this specification are indicative of the level of ordinary skill in the art to which this invention pertains.

We claim:

1. A method for the treatment of gastrointestinal injuries, diseases or ulcers, which method comprises administering to a subject to be treated an effective amount of a pharmaceutical or veterinary composition, which composition comprises:

(a) a milk product extract that contains a mixture of cell growth factors with basic to approximately neutral isoelectric points that are obtained from a milk product of an ungulate mammal by first subjecting that product to a cation exchange matrix under conditions whereby casein, alpha lactalbumin, and beta lactoglobulin present in the milk product are not absorbed to the matrix, after which the absorbed growth factor mixture is eluted and then concentrated; and (b) a pharmaceutically or veterinarily acceptable diluent, carrier or excipient therefor.

2. The method according to claim 1 wherein the gastrointestinal injuries, diseases or ulcers are selected from the group consisting of dental and oral wounds, peptic ulcers, inflammatory bowel diseases, ulcers associated with stress conditions, damage caused by radiotherapy and/or chemotherapy, inadequate gut function or damage associated with prematurity, diarrheal conditions, damage caused by food intolerance, cancer of the gastrointestinal tract, surgically induced damage, damage caused by esophageal reflux, conditions associated with loss of gut barrier function, congenital conditions resulting in inadequate gastrointestinal function or damage, and autoimmune diseases that affect the gut.

3. A method according to claim 1 wherein the cell growth factors have isoelectric points between about 6.0 and about 10.5.

* * * * *

UNITED STATES PATENT AND TRADEMARK OFFICE
CERTIFICATE OF CORRECTION

PATENT NO. : 6,447,808 B2
DATED : September 10, 2002
INVENTOR(S) : Ballard et al.

It is certified that error appears in the above-identified patent and that said Letters Patent is hereby corrected as shown below:

Column 5,
Line 66, "lactalbumin;" should read -- lactalbumin, --

Column 12,
Line 34, "yaws or" should read -- yaws or HIV --
Lines 59-60, delete second occurrence of "preferably isoelectric points between 6.0 and about 10.5"

Column 15,
Lines 42-43, delete second occurrence of "preferably isoelectric points between 6.0 and about 10.5"

Column 17,
Line 63, "(he hamster" should read -- (the hamster --

Column 20,
Line 26, "EXAMPLE7" should read -- EXAMPLE 7 --
Line 49, "x__100" should read -- x 100 --

Column 21,
Line 36, "fill" should read -- full --

Column 22,
Line 34, "camosis" should read -- carnosis --

UNITED STATES PATENT AND TRADEMARK OFFICE
CERTIFICATE OF CORRECTION

PATENT NO.    : 6,447,808 B2
DATED         : September 10, 2002
INVENTOR(S)   : Ballard et al.

It is certified that error appears in the above-identified patent and that said Letters Patent is hereby corrected as shown below:

Column 25,
Line 60, "assess" should read -- assessed --
Line 61, "was 30 based" should read -- was based --

Signed and Sealed this

Tenth Day of June, 2003

JAMES E. ROGAN
*Director of the United States Patent and Trademark Office*